US006309840B1

(12) United States Patent
Wang et al.

(10) Patent No.: US 6,309,840 B1
(45) Date of Patent: Oct. 30, 2001

(54) POLYMERASE CHAIN REACTION-RESTRICTION FRAGMENT LENGTH POLYMORPHISM TEST FOR THE AUTHENTICATION OF HERBAL CHINESE MEDICINES

(75) Inventors: Jun Wang; Pang Chi Shaw, both of Shatin; Pui-Hay Paul But, Tai Po; Fai Ngor Karenda Ngan, Kowloon, all of (HK)

(73) Assignee: The Chinese Univerisity of Hong Kong, Shatin (HK)

( * ) Notice: Subject to any disclaimer, the term of this patent is extended or adjusted under 35 U.S.C. 154(b) by 0 days.

(21) Appl. No.: 09/541,941

(22) Filed: Apr. 3, 2000

Related U.S. Application Data

(63) Continuation-in-part of application No. 09/258,111, filed on Feb. 25, 1999, now abandoned, which is a continuation of application No. 08/778,912, filed on Jan. 3, 1997, now Pat. No. 5,876,977.

(51) Int. Cl.[7] ............... C12Q 1/68; C12P 19/34; C07H 21/02; C07H 21/04
(52) U.S. Cl. ............ 435/6; 435/91.2; 536/22.1; 536/24.3
(58) Field of Search ............ 435/6, 91.2; 536/22.1, 536/24.3

(56) References Cited

U.S. PATENT DOCUMENTS 4,965,188  10/1990  Mullis et al. ............... 435/6
5,876,977   3/1999  Wang et al. ............... 435/91.2

OTHER PUBLICATIONS

David M. Hillis and Michael T. Dixon "Ribosomal DNA: Molecular Evolution And Phylogenetic Inference" *The Quarterly Review of Biology*. (1991) vol. 66 No. 4:410–449.

Wen–Sheng Lang, Zhi–Cen Lou and Paul Pui–Hay But "High–Performance Liquid Chromatographical Analysis of Ginsenosides in *Panax ginseng*, *P. quinquefalium* and *P. notoginseng*" *Journal of Chinese Pharmaceutical Sciences* (1993) pp. 133–143.

Jun Wen and Elizabeth A. Zimmer "Phylogeny and Biogeography of Panax L. (the Ginseng Genus, Araliaceae): Inferences from ITS Sequences of Nuclear Ribosomal DNA" *Molecular Phylogenetics And Evolution* (1996) vol. 6, No. 2, pp. 167–177, Article No. 0069.

*Primary Examiner*—Jeffrey Fredman
*Assistant Examiner*—Joyce Tung
(74) *Attorney, Agent, or Firm*—Cooper & Dunham, LLP; Robert D. Katz

(57) ABSTRACT

This invention provides a procedure for authentication of plant and animal materials used as traditional Chinese medicine is described. This method amplifies and detects the discrete and species-specific RFLP patterns in the region of rDNA. The present invention offers a reliable and definite way to identify morphologically similar Chinese medicine, using a minute amount of biological samples. Its application in the authentication of American and Oriental ginsengs is illustrated in detail.

2 Claims, 22 Drawing Sheets

FIG. 1

```
ACTCGCCGTT ACTAGGGGAA TCCTTGTAAG TTTCTTTTCC TCCGCTTATT GATATGCTTA
AACTCAGCGG GTAGTCCCGC TGACCTGGGG TCGCGGTCGG AGCGCACGTC GAGGAGCGCA
ACAGGGTCAT GAGAGCTTTT GCTGGCGACG GGTCACCGCA CGACATGAGA AGAGGGCTTT
TTACAACCAC CACTTGTCGT GACGTCCATC GCCAAGGACT CGCATTTGGG CCAACCGCGC
GGTGAGACAC GGGAGGCCAT TATCCGCCCC TCCGCCTCGA CTCCCGCAAA GGAGTGATGG
GTTGGGGGGC GACGCGATGC GTGAACGCCC AGGCAGACGT GCCCTCGGCC TAATGGCTTC
GGGCGCAACT TGCGTTCAAA GACTCGATGG TTCACGGGAT TCTGTAATTC ACACCAAGTA
TCGCATTTCG CTACGTTCTT CATCGATGCG AGAGCCGAGA TATCCGTTGC CGAGAGTCGT
TTGTGTTTTA GAAAGACGCT TCCGCCGCCC GCAAACGGGG GGGACGCGTG CAGTTCAGTT
TGATTTCCTT GGCGCATTCC GCGCCGGGGG GTCGTTGTTC GGACGAGAGC CACCCAAGGG
TGGTCCCCGA CCATGGGTTT GCAACTTGGG GAGCTTGCGC ACCCCTCGTC CCTCACCCGG
TATTGTAACG TGTTCGCGGG TCGTTCTGCT ATGCAGGTTT CGACAATGAT CCTTCCGCAG
GTTCACCTAC GGAAACCTTG TTACGACTTC TCCTTCCTCT AAATGATAAG GTTCAGTGGA
CTTCTTTCGA CGTCGCGGGC AGCGAACCGC CCACGTCGCC GCAATCCGAA CACTTCACCG
GACCATTCAA TCGGTAGGAG CGACGGGCGG TGTG
```

FIG. 2A

```
ACTCGCCGTT ACTAGGGGAA TCCTTGTAAG TTTCTTTTCC TCCGCTTATT GATATGCTTA
AACTCAGCGG GTAGTCCCGC TGACCTGGGG TCGCGGTCGG AGCGCACGTC GAGGACGGCG
CAACAGGGTC ATGAGAGCTT TTGCTGGCGA CGGGTCACCG CACGACATGA GAAGAGGGCT
TTTTACAACC ACCACTTGTC GTGACGTCCA TCGCCAAGGA CTCGCATTTG GCCAACCGC
GCGGTGAGAC ACGGGAGGCC ATTATCCGCC CCTCCGCCTC AACTCCCGCA AGGGAGTGAT
GGGTTGGGGG GCGACGCGAT GCGTGACGCC CAGGCAGACG TGCCCTCGGC CTAATGGCTT
CGGGCGCAAC TTGCGTTCAA AGACTCGATG GTTCACGGGA TTCTGCAATT CACACCAAGT
ATCGCATTTC GCTACGTTCT TCATCGATGC GAGACGCGAG ATATCCGTTG TCGAGAGTCG
TTTGTGTTTT AGAAAGACGC TTCCGCCGCC CGCAAACGGG GGGACGCGT GCAGTTCAGT
TTGATTTCCT TGGCGCATTC CGCGCCGGGG GGTCGTTGTT CGGACGAGAT CCACCCAAGG
GTGGTCCCCG ACCATGGGTT TGCAACTTGG GGAGCTTGCG CACCCCTCGT CCCTCACCCG
GTATTGTAAC GTGTTCGCGG GTCGTTCTGC TATGCAGGTT TCGACAATGA TCCTTCCGCA
GGTTCACCTA CGGAAACCTT GTTACGACTT CTCCTTCCTC TAAATGATAA GGTTCAGTGG
ACTTCTTTCG ACGTCGCGGG CAGCGAACCG CCCACGTCGC CGCAATCCGA ACACTTCACC
GGACCATTCA ATCGGTAGGA GCGACGGGCG GTGTG
```

FIG. 2B-1

```
                    10         20         30         40         50
G1.DNA      1  ACTCGCCGTT ACTAGGGGAA TCCTTGTAAG TTTCTTTTCC TCCGCTTATT    5
IC.DNA      1  ACTCGCCGTT ACTAGGGGAA TCCTTGTAAG TTTCTTTTCC TCCGCTTATT    5

60         70         80         90        100
G1.DNA     51  GATATGCTTA AACTCAGCGG GTAGTCCCGC -TGACCTGGG GTCGCGGTCG   10
IC.DNA     51  GATATGCTTA AACTCAGCGG GTAGTCCCGC CTGACCTGGG GTCGCGGTCG   10
                                                1

110        120        130        140        150
G1.DNA    101  GAGCGCACGT CGAGGACGGC GCAACAGGGT CATGAGAGCT TTTGCTGGCG   15
IC.DNA    101  GAGCGCACGT CGAGAGACGC GCAACAGGGT CATGAGAGCT TTTGCTGGCG   15

160        170        180        190        200
G1.DNA    151  ACGGGTCACC GCACGACATG AGAAGAGGGC TTTTTACAAC CACCACTTGT   20
IC.DNA    151  ACGGGTCACC GCACGACATG AGAAGAGGGC TTTTTACAAC CACCACTTGT   20

210        220        230        240        250
G1.DNA    201  CGTGACGTCC ATGCCAAGG  ACTCGCATTT GGGCCAACCG CGGGGTGAGA   25
IC.DNA    201  CGTGACGTCC ATGCCAAGG  ACTCGCATTT GGGCCAACCG CGCGGTGAGA   25

260        270        280        290        300
G1.DNA    251  CACGGGAGGC CATTATCCGC CCCTCCGCCT CAACTCCCGC AAGGGAGTGA   30
IC.DNA    251  CACGGGAGGC CATTATCCGC CCCTCCGCCT CAACTCCCGC AAGGGAGTGA   30

310        320        330        340        350
G1.DNA    301  TGGGTTGGGG GGCGACGCGA TGCGTGACGC CCAGGCAGAC GTGCCCTCGG   35
IC.DNA    301  TGGGTTGGGG GGCGACGCGA TGCGTGACGC CCAGGCAGAC GTGCCCTCGG   35

360        370        380        390        400
G1.DNA    351  CCTAATGGCT TCGGGCGCAA CTTGCGTTCA AAGACTCGAT GGTTCACGGG   40
IC.DNA    351  CCTAATGGCT TCGGGCGCAA CTTGCGTTCA AAGACTCGAT GGTTCACGGG   40

410        420        430        440        450
G1.DNA    401  ATTCTGCAAT TCACACCAAG TATGCCATTT CGCTACGTTC TTCATCGATG   45
IC.DNA    401  ATTCTGCAAT TCACACCAAG TATGCCATTT CGCTACGTTC TTCATCGATG   45
```

FIG. 2B-2

```
            460        470        480        490        500
G1.DNA  451 CGAGAGCGA GATATCCGTT GTCGAGAGTC GTTTGTGTTT TAGAAAGACG  50
IC.DNA  451 CGAGAGCCGA GATATCCGTT GCCGAGAGTC GTTTGTGTTT TAGAAAGACG  50

510        520        530        540        550
G1.DNA  501 CTTCCGCCGC CCGCAAACGG GGGGGACGCG TGCAGTTCAG TTTGATTTCC  55
IC.DNA  501 CTTCCGCCGC CCGCAAACGG GGGGGACGCG TGCAGTTCAG TTTGATTTCC  55

560        570        580        590        600
G1.DNA  551 TTGGCGCATT CCGCGCCGGG GGGTCGTTGT TCGGACGAGA TCCACCCAAG  60
IC.DNA  551 TTGGCGCATT CCGCGCCGGG GGGTCGTTGT TCGGACGAGA TCCACCCAAG  60

610        620        630        640        650
G1.DNA  601 GGTGGTCCCC GACCATGGGT TTGCAACTTG GGGAGCTTGC GCACCCCTCG  65
IC.DNA  601 GGTGGTCCCC GACCATGGGT TTGCAACTTG GGGAGCTTGC GCACCCCTCG  65

660        670        680        690        700
G1.DNA  651 TCCCTCACCC GGTATTGTAA CGTGTTCGCG GGTCGTTCTG CTATGCAGGT  70
IC.DNA  651 TCCCTCACCC GGTATTGTAA CGTGTTCGCG GGTCGTTCTG CTATGCAGGT  70

710        720        730        740        750
G1.DNA  701 TTCGACAATG ATCCTTCCGC AGGTTCACCT ACGGAAACCT TGTTACGACT  75
IC.DNA  701 TTCGACAATG ATCCTTCCGC AGGTTCACCT ACGGAAACCT TGTTACGACT  75

760        770        780        790        800
G1.DNA  751 TCTCCTTCCT CTAAATGATA AGGTTCAGTG GACTTCTTTC GACGTCGCGG  80
IC.DNA  751 TCTCCTTCCT CTAAATGATA AGGTTCAGTG GACTTCTTTC GACGTCGCGA  80

810        820        830        840        850
G1.DNA  801 GCAGCGAACC GCCCAGTCG CCGCAATCCG AACACTTCAC CGGACCATTC  85
IC.DNA  801 GCAGCGAACC GCCCAGTCG CCGCAATCCG AACACTTCAC CGGACCATTC  85

860        870        880        890        900
G1.DNA  851 AATCGGTAGG AGCGACGGC GGTGTG....  ........   ........    90
IC.DNA  851 AATCGGTAGG AGCGACGGGG ........    ........   ........    90
```

FIG. 3

```
ACTCGCCGTT ACTAGGGGAA TCCTTGTAAG TTTCTTTTCC TCCGCTTATT GATATGCTTA
AACTCAGCGG GTAGTCCCGC CTGACCTGGG GTCGCGGTCG GAGCGCACGT CGAGGACGGC
GCAACAGGGT CATGAGAGCT TTTGTTGGCG AAGGGTCACC GCACGACATG AGAAGAGGGC
TTTTTACAAC CACCACTTGT CGTGACGTCC ATCGCCAAGG ACTCGCATTT GGGCCAACCG
CACGGTGAGA CACGGGAGGC CAATATCCGC CCCTCCGCCT CGACTCCCGC AAGGGAGTGA
TGGGTTGGGG GGCGACGCGA TGCGTGAACG CCCAGGCAGA CGTGCCCTCG GCCTAATGGC
TTAGGGCGCA ACTTGCGTTC AAAGACTCGA TGGTTCACGG GATTCTGCAA TTCACACCAA
GTATCGCATT TCGCTACGTT CTTCATCGAT GCGAGAGCCG AGATATCCGT TGCCGAGAGT
CGTTTGTGTT TTAGAAAGAC GCTTCCGCCG CCCGCAAATG GGGGGACGC GTGCAGTTCA
GTTTGATTTC CTTGGCACAT TCCGCGCCGG GGGGTCGTTG TTCGGACGAG ATCCACCAAG
GGTGTCCCCG ACCATGGGTT TGCAACTTGG GGAGCTTGCG CACGCCTCGT CCCTCACCCG
GTATTGTAAC GTGTTCACGG GTCGTTCTGC TATGCAGGTT TCGACAATGA TCCTTCCGCA
GGTTCACCTA CGGAAACCTT GTTACGACTT CTCCTTCCTC TAAATGATAA GGTTCAGTGG
ACTTCTTTCG ACGTCGCGGG CAGCGAACCG CCCACGTCGC CGCAATCCGA ACACTTCACC
GGACCATTCA ATCGGTAGGA GCGACGGGCG GTGTG
```

FIG. 4

```
ACTCGCCGTT ACTAGGGGAA TCCTTGTAAG TTTCTTTTCC TCCGCTTATT GATATGCTTA
AACTCAGCGG GTAGTCCCGC TGACCTGGGG TCGCGGTCGG AGCGCACGTC GAGGACGGCG
CAACAGGGTC ATGAGAGCTT TTGCTGGCGA CGGGTCACCG CACGACATGA GAAGAGGGCT
TTTTACAACC ACCACTTGTC GTGACGTCCA TCGCCAAGGA CTCGCATTTG GCCAACCGC
GCGGTGAGAC ACGGGAGGCC ATTATCCGCC CCTCCGCCTC GACTCCCGCA AAGGAGTGAT
GGGTTGGGGG GCGACGCGAT GCGTGAACGC CCAGGCAGAC GTGCCCTCGG CCTAATGGCT
TCGGGCGCAA CTTGCGTTCA AAGACTCGAT GATTCACGGG ATTCTGCAAT TCACACCAAG
TATCGCATTT CGCTACGTTC TTCATCGATG CGAGAGCCGA GATATCCGTT GCCGAGAGTC
GTTTGTGTTT TAGAAAGACG CTTCCGCCGC CCGCAAACGG GGGGACGCG TGCAGTTCAG
TTTGATTTCC TTGGCGCATT CCGCGCCGGG GGTCGTTGT TCGGACGAGA GCCACCCAAG
GGTGGTCCCC GACCATGGGT TTGCAACTTG GGGAGCTTGC GCACCCCTCG TCCCTCACCC
GGTATTGTAA CGTGTTCGCG GGTCGTTCTG CTATGCAGGT TTCGACAATG ATCCTTCCGC
AGGTTCACCT ACGGAAACCT TGTTACGACT TCTCCTTCCT CTAAATGATA AGGTTCAGTG
GACTTCTTTC GACGTCGCAG GCAGCGAACC GCCCACGTCG CCGCAATCCG AACACTTCAC
CGGACCATTC AATCGGTAGG AGCGACGGGC GGTGTG
```

FIG. 5

```
ACTCGCCGTT ACTAGGGGAA TCCTTGTAAG TTTCTTTTCC TCCGCTTATT GATATGCTTA
AACTCAGCGG GTAGTCCCGC CTGACCTGGG GTCGCGGTCG GAGCGCGCGT CGGGGACGGC
GCAACAGGGT CGTGAGAGCC TTTGCCGGCG ACGGGTCACC GCACGACTTG AGAAGAGGGC
TTTTTACAAC CACCACTTGT CGTGACGTCC GTCGCCGAGG ACTCGCATTT GGGCCAACCG
CGCGGTTAGA CACGGGAGGC CAATATCCGC CCCTCCGCCT CGACTCCCGT AAGGGAGTGA
TGGGTTGGGG GGCGACGCGA TGCGTGACGC CCAGGCAGAC GTGCCCTCGG CCTAATGGCT
TAGGGCGCAA CTTGCGTTCA AAGACTCGAT GGTTCACGGG ATTCTGCAAT TCACACCAAG
TATCGCATTT CGCTACGTTC TTCATCGATG CGAGAGCCGA GATATCCGTT GCCGAGAGTC
GTTTGTGTTT TAGAAAGACG CTTCCGCCGC CCGCAAACGG GGGGACGCG TGCAGTTCAG
TTTGATTTCC TTGGCGCATT CCGCGCCGGG GGTCGTTGT TCGGACGGGG AGCACCCGGG
GGCGGCCCCC GACCATGGGT TCGGAACTTG GGGGCTTGC GCACCCTTCG TCCCTCACCC
GGTGTTGAAA CGTGTTCGCG GGTCGTTCTG CTGTGCAGGT TTCGACAATG ATCCTTCCGC
AGGTTCACCT ACGGAAACCT TGTTACGACT TCTCCTTCCT CTAAATGATA AGGTTCAGTG
GACTTCTTTC GACGTCGCGG CAGCGAACCG CCCACGTCGC CGCAATCCGA ACACTTCACC
GGACCATTCA ATCGGTAGGA GCGACGGGCG GTGTG
```

FIG. 6

5' AGCCATCCTCGCTGCCCGCCACAC 3'

3' ACTCGCCGTTACTAGGGGAA 5'

Figure 10

| | E. brevicornum | E. koreanum | E. pubescens | E. wushanense |
|---|---|---|---|---|
| HgaI (↓N₁₀GCGTC) | 589 | 589 | 589 | /* |
| Resultant Fragments produced in bp | <u>309, 589</u>** | <u>309, 589</u> | <u>309, 589</u> | <u>898</u> |
| HinfI (G↓ANTC) | 18,399,416,492,586,650 | 18,399,416,586,650 | 18,399,416,492,586,650 | 18,399,416,492,586,650 |
| Resultant Fragments produced in bp | 17,18,64,<u>76,94</u>,248,381 | 17,18,64,<u>170</u>,248,381 | 17,18,64,<u>76,94</u>,248,381 | 17,18,64,<u>76,94</u>,248,381 |
| HpaI (GTT↓AAC) | / | / | / | 658 |
| Resultant Fragments produced in bp | 898 | 898 | 898 | <u>240, 658</u> |
| MaeII (A↓CGT) | 284,355,451,531,814,837 | 284,355,451,531,814,837 | 284,355,451,531,814,837 | 284,355,451,531,599,814,837 |
| Resultant Fragments produced in bp | 23,61,71,80,96,283,284 | 23,61,71,80,96,283,284 | 23,61,71,80,96,283,284 | 23,61,<u>68</u>,71,80,96,<u>215</u>,284 |
| MseI (T↓TAA) | 58,545 | 58,545 | 58,545 | 58,545,659 |
| Resultant Fragments produced in bp | 58,<u>353</u>,487 | 58,<u>353</u>,487 | 58,<u>353</u>,487 | 58,<u>114,239</u>,487 |
| PleI (GAGTCN₄↓) | 492 | / | 492 | 492 |
| Resultant Fragments produced in bp | <u>406,492</u> | <u>898</u> | <u>406,492</u> | <u>406,492</u> |

- * absence of restricton sites.
- ** polymorphic fragments are underlined

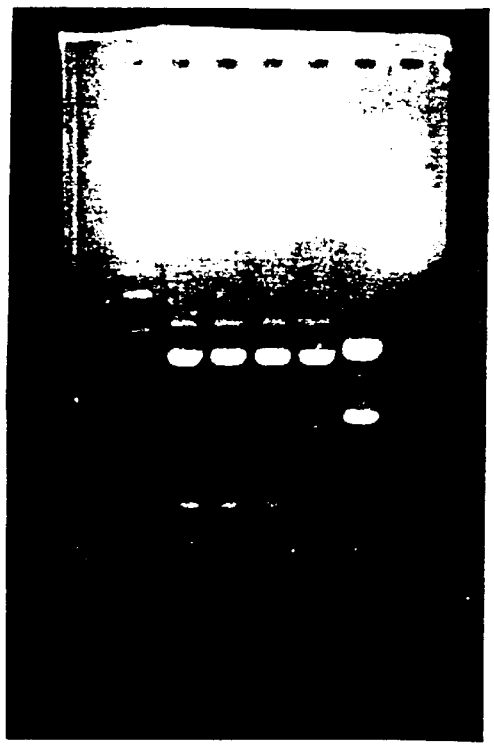
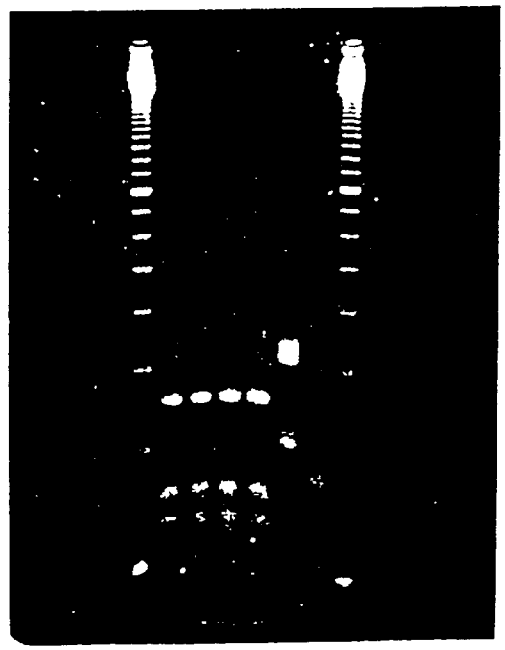
Figure 11

Source: Codonopsis modesta  918 bp  DNA

```
  1 CACACCGCCC GTCGTCCTA CCGAAGGACC GGTCCGGGTG TGTTGGGTTC GCGGCGACCT
 61 GGGCGGTTCG CCGCCGGCGA CGTCGCGAGA AGTCCACTGA ACCTTATCAT TTAGAGGAAG
121 GAGAAGTCGT AACAAGGTTT CCGTAGTGAA CCTGCGGAAG GATCATTGTC GAAACCTGCA
181 CAGCAGAACG ACCCGCGAAC ACGTGAACAA CACCGGGGAC GCGGGCTTGC CCGTGGCCCC
241 TTGCCGTCGG CGCATGCACC CGCCCAACCA CTTGGTGGAA GGGAGCATGC GTGCGTCGTT
301 CGGCGCCAAA CGAACCCGC GCGATCCGCG CCAAGGAAAA CTTAACTCAA AGAGCGCCAC
361 GTCCTCCCGT CGCCCGTTC GCGGTGTGCG CACGGTTGGG TGGTCGCTTC TTAGTGAAAA
421 ACACAAACGA CTCTCGGCAA CGGATATCTC GGCTCTCGCA TCGATGAAGA ACGTAGCGAA
481 ATGCGATACT TGGTGTGAAT TGCAGAATCC CGTGAACCAT CGAGTCTTTG AACGCAAGTT
541 GCGCCCGAAG CCGTTAGGGC GAGGGCACGT CTGCATGGGC GTCACGCATC GCGTCGCCTC
601 CCTTATGATA ATTTTGTTTA CGTTAACAAG TAACGGAAAG GGGGAGCGGA TACTGGCCTC
661 CCGTGCCTTG CGGCGCGGCT GGCTCAAAAC GGAGTCCCCG CGAAGGACGC ACGACAAGTG
721 GTGGTTGATA ACAACCCCTC GCGTCCTATC GTGCGCACGT CCTGCGATGG GTTGGCTCTC
781 GTGACCCTGA CGCGTCTAGG TCTAAGCCTA AGGCGCTCCG ACCGCGACCC CATGTCAGGC
841 GGGACTACCC GCTGAGTTTA AGCATATCAA TAAGCGGAGG AAAGAAACT TACAAGGATT
901 CCCCTAGTAA CGGCGAGT
```

Figure 13B

Source: Codonopsis nervosa  918 bp  DNA

```
  1 CACACCGCCC GTCGTCCTA CCGAAGGACC GGTCCGGGTG TGTTGGGTTC GCGGCGACCT
 61 GGGCGGTTCG CCGCCGGCGA CGTCGCGAGA AGTCCACTGA ACCTTATCAT TTAGAGGAAG
121 GAGAAGTCGT AACAAGGTTT CCGTAGTGAA CCTGCGGAAG GATCATTGTC GAAACCTGCA
181 CAGCAGAACG ACCCGCGAAC ACGTGAATAA CACCGGGGAC GCGGGATTGC CCGTGGCCCT
241 TTGCCGTCGG CGCATGCACC CGCCCAACCA CTTGGTGGAA GGGAGCATGC GTGCGTCGTT
301 CGGCGCCAAA CGAACCCGC GCGATCCGCG CCAAGGAAAA CTTAACTCAA AGAGCGCCAC
361 GTCCTCCCGT CGCCCGTTC GCGGTGTGCG CACGGTTGGG TGGTCGCTTC TTAGTGAAAA
421 ACACAAACGA CTCTCGGCAA CGGATATCTC GGCTCTCGCA TCGATGAAGA ACGTAGCGAA
481 ATGCGATACT TGGTGTGAAT TGCAGAATCC CGTGAACCAT CGAGTCTTTG AACGCAAGTT
541 GCGCCCGAAG CCGTTAGGGC GAGGGCACGT CTGCATGGGC GTCACGCATC GCGTCGCCTC
601 GTTTATGATA ATTTTGTTTA CGTTAACAAG TAACGGAAAG GGGGAGCGGA TACTGGCCTC
661 CCGTGCCTTG CGGCGCGGCT GGCTCAAAAC GGAGTCCCCG CGAAGGACGC ACGACAAGTG
721 GTGGTTGATA ACAACCCCTC GCGTCCTATC GTGCGCACGT CCTGCGATGG GTTGGCTCTC
781 GTGACCCTGA CGCGTCTAGG TCTAAGCCTA AGGCGCTCCG ACCGCGACCC CATGTCAGGC
841 GGGACTACCC GCTGAGTTTA AGCATATCAA TAAGCGGAGG AAAGAAACT TACAAGGATT
901 CCCCTAGTAA CGGCGAGT
```

Figure 13C

Source: *Codonopsis pilosula*　　　　　917 bp　　DNA

```
  1 CACACCGCCC GTCGCTCCTA CCGAAGGACC GGTCCGGGTG TGTTGGGTTC GCGGCGACCT
 61 GGGCGGTTCG CCGCCGGCGA CGTCGCGAGA AGTCCACTGA ACCTTATCAT TTAGAGGAAG
121 GAGAAGTCGT AACAAGGTTT CCGTAGTGAA CCTGCGGAAG GATCATTGTC GAAACCTGAC
181 AGCAGAACGA CCCGCGAACA CGTGAACAAC ACCGGGGACG CGGGCTTGCC CGTGGCCCCT
241 TGCCGTCGGC GCATGCACCC GCCCAACCAC TTGGTGGAAG GGAGCATGCG TGCGTCGTTC
301 GGCGCCAAAC GAACCCCGCG CGATCCGCGC CAAGGAAAAC TTAACTCAAA GAGCGCCACG
361 TCCTCCCGTC GCCCCGTTCG CGGTGTGCGC ACGGTTGGGT GGTCGCTTCT TAGTGAAAAA
421 CACAAACGAC TCTCGGCAAC GGATATCTCG GCTCTCGCAT CGATGAAGAA CGTAGCGAAA
481 TGCGATACTT GGTGTGAATT GCAGAATCCC GTGAACCATC GAGTCTTTGA ACGCAAGTTG
541 CGCCCGAAGC CGTTAGGGCG AGGGCACGTC TGCATGGGCG TCACGCATCG CGTCGCCTCC
601 CTTATGATAA TTTTGTTTAC GTTAACAAGT AACGGAAAGG GGGAGCGGAT ACTGGCCTCC
661 CGTGCCTTGC GGCGCGGCTG GCTCAAAACG GAGTCCCCGC GAAGGACGCA CGACAAGTGG
721 TGGTTGATAA CAACCCCTCG CGTCCTATCG TGCGCACGTC CTGCGATGGG TTGGCTCTCG
781 TGACCCTGAC GCGTCTAGGT CTAAGCCTAA GGCGCTCCGA CCGCGACCCC ATGTCAGGCG
841 GGACTACCCG CTGAGTTTAA GCATATCAAT AAGCGGAGGA AAAGAAACTT ACAAGGATTC
901 CCCTAGTAAC GGCGAGT
```

Figure 13D

Source: *Codonopsis tangshen*　　　　　918 bp　　DNA

```
  1 CACACCGCCC GTCGCTCCTA CCGAAGGACC GGTCCGGGTG TGTTGGGTTC GCGGCGACCT
 61 GGGCGGTTCG CCGCCGGCGA CGTCGCGAGA AGTCCACTGA ACCTTATCAT TTAGAGGAAG
121 GAGAAGTCGT AACAAGGTTT CCGTAGTGAA CGTGCGGAAG GATCATTGTC GAAACCTGCA
181 CAGCAGAACG ACCCGCGAAC ACGTGAACAA CACCGGGGAC GCGGGCTTGC CCGTGGCCCC
241 TTGCCGTCGG CGCATGCACC CGCCCAACCA CTTGGTGGAA GGGAGCATGC GTGCGTCGTT
301 CGGCGCCAAA CGAACCCCGC GCGCTCCGCG CCAAGGAAAA CTTAACTCAA AGAGCGCCAC
361 GTCCTCCCGT CGCCCCGTTC GCGGTGTGCG CACGGTTGGG TGGTCGCTTC TTAGTGAAAA
421 ACACAAACGA CTCTCGGCAA CGGATATCTC GGCTCTCGCA TCGATGAAGA ACGTAGCGAA
481 ATGCGATACT TGGTGTGAAT TGCAGAATCC CGTGAACCAT CGAGTCTTTG AACGCAAGTT
541 GCGCCCGAAG CCGTTAGGGC GAGGGCACGT CTGCATGGGC GTCACGCATC GCGTCGCCTC
601 CCTTATGATA ATTTTGTTTA CGTTAACAAG TAACGGAAAG GGGGAGCGGA TACTGGCCTC
661 CCGTGCCTTG CGGCGCGGCT GGCTCAAAAC GGAGTCCCCG CGAAGGACGC ACGACAAGTG
721 GTGGTTGATA ACAACCCCTC GCGTCCTATC GTGCGCACGT CCTGCGATGG GTTGGCTCTC
781 GTGACCCTGA CGCGTCTAGG TCTAAGCCTA AGGCGCTCCG ACCGCGACCC CATGTCAGGC
841 GGGACTACCC GCTGAGTTTA AGCATATCAA TAAGCGGAGG AAAAGAAACT TACAAGGATT
901 CCCCTAGTAA CGGCGAGT
```

Figure 13E

Source: *Platycodon grandiflorus*    815 bp    DNA

```
  1 TAGAGGAAGG AGAAGTCGTA ACAAGGTTTC CGTAGTGCAC CTGCGGAAGG ATCAGTGTCG
 61 AAACTGCACA GCAGCGCGTT CGCCAACGCA TGAACAACAC CGGGGTCTCG GGCTTGCCCG
121 TGGCGCCTAC GCGTCGCCGC ATGCACCCAT TCAACCACTT GGTGGAAGGG AGTATGAGTG
181 CGTCGTTCGG CGGCAAACGA ACCCCGCGAT CCATTTTAAG GAGAACTTAA CTCAAGCGTA
241 GAGCTCCACG TGTCATCCCG TCGAACCGTT CGCGGTGTCC GCACGGTTAA GTGGTCGCTT
301 CTTAGTGAAA AGCAAACGAC TGTCGGCAAC GGATATCTCG GCTCTCGCAT CGATGAAGAA
361 CGTAGCGAAA TGCGATACTT GGTGTGAATT GCAGAATACC GTGAACCATC GAGCCTTTGA
421 ACGCAAGTTG CGCCCGAAGC CGTTAGGGCG AAGCACGTC TGCATGGGCG TCACGCATCG
481 CGTCGCCTCC CATTATGATA GATTTGTGTA CGTTAATAAG TCAATACAGG AAAGGGGGTG
541 CGGATAGAGG CCTCCCGTGC CTAGCGGCGG CGTGGCTGGC TCAAAACGGA GTTCCCGCGA
601 AGGGCGCACG ACAAGTGACG GTCGATAACA ACCCCGAGCT TCCTATCGAG CCCACGTCCT
661 GCGATGGGTT GGCGCTCGTG ACCCTGACGC GTCTAGGTCT CATGCTAAGG CGCTCAGACC
721 GCGACTCCAT GTCAGGCGGG ACTACCCGCT GAGTTTAAGC ATATCAATAA GCCGAGGAAA
781 ACAAACTTAC AACCATTCCC CTACTAACCC CCAGT
```

Figure 13F

Source: *Campanumoea javanica*    904 bp    DNA

```
  1 CACACCGCCC GTCGCTCCTA CCGAAGGACC GGTCCGGGTG TGTTGGGTTC GCGCCGACCT
 61 GGGCGGTTCG CCGTTGGCGA CGTCGCGAGA AGTCCACTGA ACCTTATCAT TTAGAGGAAG
121 GAGAAGTCGT AACAAGGTTT CCGTAGAGAA CCTGCGGAAG GATCGTTGTC GAAACCTGCA
181 CAGCAGAACG ACCCGCGAAC ACATGAACGA CACCGACGC GGGCTTGCCC GTGGCCCATG
241 CCGTCGGTCC ATGCACCCCA ACCTCTTGGT GGAAATGAGC ATGCAGTGCG TAATTCGGCG
301 TCAAACGAAC CTCGCGATCC GTGCCAAGGA GCTTAACTCC AAGAGCTCCA CGTCCTCCCG
361 GCGCCCGTTC GCGGTGTGCG TACGGTTGGG TGGTCGCTTC TTAGGAAAA ACTCAAACGA
421 CTTTCGGCAA CGGATATCTC GACTCTCGCA TCGATGAAGA ACGTAGCGAA ATGCGATACT
481 TGGTGTGAAT TGCAGAATCC CGTGAACCAT CGAGTCTTTG AACGCAAGTT CCGCCCGAAG
541 CCGTTAGGGC GAGGGCGAGT CTGCATGGGC GCCACGCATC GCGTCGCTCC CACCATGATG
601 CCTTTGTTCT GTTATCGGGC AACGCAACGT GGGAAGCGGA TATTGGCCCC CCGTACCTTT
661 GTGCGGCGTG GCCTTCAAAA CGGCCTCGCG AACGACGTAC GATCAGTGGT GGTTGATAAC
721 CCCTTTGCGT CATATCGTGC GTACGTGTTG CGATGGGTTG GCTATCGTGA CCCTGACGCG
781 TCTACGTACA AGCCTAACGC GTTCCGACTG CGACCCCATG TCAGGCGGGA CTACCCGCTG
841 AGTTTAAGCA TATCAATAAG CGGAGGAGAA GAGACTTACA AGGATTCCCC TAGTAACGGC
901 GAGT
```

Figure 13G

```
Epimedium brevicornum    898 bp
   1 ACTCGCCGTT ACTAGGGGAA TCCTTGTAAG TTTCTTCTCC TCCGCTTATT GATATGCTTA
  61 AACTCAGCGG GTAGTCCCGC TGACCTGGGG TCGCAGAGTG AATGTCGTTT ATACGACACG
 121 CAAGGGTCCA TATGGCCCAA ATAGACGACG AAACAACACG ATACCGGTCT ATGACAAAGG
 181 GGTTATTCAA CCACCACTGA TCGTGACGCT CGTCGCCGAG GGCCGAATTT TAGGCCGGCC
 241 GCGCCTACAA AGGTACGGGG GGCCAATATC CGCTTCCCAA ACCACGTTGC AGTTGCCCGA
 301 TAACAAAACA AAGGCATCAT GGTGGGAGCG ACGCTGTGGC TGACGCCCAG GCAGACGTGC
 361 CCTCGACCTA ATGGCCTTGG GCGCAACTTG CGTTCAAAGA CTCGATGGTT CACGGGATTC
 421 TGCAATTCAC ACCAAGTATC GCATTTCGCT ACGTTCTTCA TCGATGCGAG AGCCGAGATA
 481 TCCATTGCCG AGAGTCGTTA TAAGATCGGA ATTACAACAT CGTCATGAAG ACGTGCTCTA
 541 TCCGTTAAGA TTTTCCTTGG CGCAGACCGC GCCGAGTTGT TATTTGAATC AACGAGGGGC
 601 GTCGTTCTCG CTTTCACGAC ACAATCGTCC CAAGTGACCC AGTAGGAAGG ATTCAAGGTT
 661 AGCACCCTTC GTCCCTCCCA CAAGTGTTTT TCACAAGTTC GCTGGTCGTT CTGCTTTGCA
 721 GGTTTTGACA ATGATCCTTC CGCAGGTTCA CTACGGAAAC CTTGTTACGA CTTCTCCTTC
 781 CTCTAAATGA TAAGGTTCAA TGGACTTCTC GCGACGTCGC CGGCGGCGAA CCACCCACGT
 841 CGCCGCGATC CGAACATTTC ACCGGACCAT TCAATCGGTA GGAGCGACGG GCGGTGTG
```

Figure 13H

```
Epimedium koreanum    898 bp
   1 ACTCGCCGTT ACTAGGGGAA TCCTTGTAAG TTTCTTCTCC TCCGCTTATT GATATGCTTA
  61 AACTCAGCGG GTAGTCCCGC TGACCTGGGG TCGCAGAGTG AATGTCGTTT ATACGACACG
 121 CAAGGGTCCA TATGGCCCAA ATAGACGACG AAACAACACG ATACCGGTCT ATGACAAAGG
 181 GGTTATTCAA CCACCACTGA TCGTGACGCT CGTCGCCGAG GGCCGAATTT TAGGCCGGCC
 241 GCGCCTACAA AGGTACGGGG GGCCAATATC CGCTTCCCAA GCCACGTTGC AGTTGCCCGA
 301 TAACAGAACA AAGGCATCAT GGTGGGAGCG ACGCTGTGGC TGACGCCCAG GCAGACGTGC
 361 CCTCGACCTA ATGGCCTTGG GCGCAACTTG CGTTCAAAGA CTCGATGGTT CACGGGATTC
 421 TGCAATTCAC ACCAAGTATC GCATTTCGCT ACGTTCTTCA TCGATGCGAG AGCCGAGATA
 481 TCCATTGCCG AGGGTCGTTA TAAGATCGGA ATTACAACAT CGTCATGAAG ACGTGCTCTA
 541 TCCGTTAAGA TTTTCCTTGG CGCAGACCGC GCCGAGTTGT TATTTGAATC AACGAGGGGC
 601 GTCGTTGTCG CTTTCACGAC ACAATCGTCC CAAGTGACCC AGTAGGAAGG ATTCAAGGTT
 661 AGCACCCTTC GTCCCTCCCA TAAGTGTTTT TCACAAGTTC GCTGGTCGTT CTGCTTTGCA
 721 GGTTTTGACA ATGATCCTTC CGCAGGTTCA CTACGGAAAC CTTGTTACGA CTTCTCCTTC
 781 CTCTAAATGA TAAGGTTCAA TGGACTTCTC GCGACGTCGC CGGCGGCGAA CCACCCACGT
 841 CGCCGCGATC CGAACATTTC ACCGGACCAT TCAATCGGTA GGAGCGACGG GCGGTGTG
```

Figure 13I

```
Epimedium pubescens 898 bp
     1 ACTCGCCGTT ACTAGGGGAA TCCTTGTAAG TTTCTTCTCC TCCGCTTATT GATATGCTTA
    61 AACTCAGCGG GTAGTCCCGC TGACCTGGGG TCGCAGAGTG AATGTCGTTT ATACGACACG
   121 CAAGGGTCCA TATGGCCCAA ATAGACGACG AAACAACACG ATACCGGTCT ATGACAAAGG
   181 GGTTATTCAA CCACCACTGA TCGTGACGCT CGTCGCCGAG GGCCGAATTT TAGGCCGGCC
   241 GCGCCTACAA AGGTACGGGG GGCCAATATC CGCTTCCCAA GCCACGTTGC AGTTGCCCGA
   301 TAACAGAACA AAGGCATCAT GGTGGGAGCG ACGCTGTGGC TGACGCCCAG GCAGACGTGC
   361 CCTCGACCTA ATGGCCTTGG GCGCAACTTG CGTTCAAAGA CTCGATGGTT CACGGGATTC
   421 TGCAATTCAC ACCAAGTATC GCATTTCGCT ACGTTCTTCA TCGATGCGAG AGCCGAGATA
   481 TCCATTGCCG AGAGTCGTTA TAAGATCGGA ATTACAACAT CGTCATGAAG ACGTGCTCTA
   541 TCCGTTAAGA TTTTCCTTGG CGCAGACCGC GCCGAGTTGT TATTTGAATC AACGAGGGGC
   601 GTCGTTGTCG CTTTCACGAC ACAATCGTCC CAAGTGACCC AGTAGGAAGG ATTCAAGGTT
   661 AGCACCCTTC GTCCCTCCCA TAAGTGTTTT TCACAAGTTC GCTGGTCGTT CTGCTTTGCA
   721 GGTTTTGACA ATGATCCTTC CGCAGGTTCA CTACGGAAAC CTTGTTACGA CTTCTCCTTC
   781 CTCTAAATGA TAAGGTTCAA TGGACTTCTC GCGACGTCGC CGGCGGCGAA CCACCCACGT
   841 CGCCGCGATC CGAACATTTC ACCGGACCAT TCAATCGGTA GGAGCGACGG GCGGTGTG
```

Figure 13J

```
Epimedium wushanense      898 bp
     1 ACTCGCCGTT ACTAGGGGAA TCCTTGTAAG TTTCTTCTCC TCCGCTTATT GATATGCTTA
    61 AACTCAGCGG GTAGTCCCGC TGACCTGGGG TCGCAGAGTG AATGTCGTTT ACACGACACG
   121 CAAGGGTCCA TATGGCCCAA ATAGACGACG AAACAACACG ATACCGGTCT ATGACAAAGG
   181 GGTTATTCAA CCACCACTGA TCGTGACGCT CGTCGCCGAG GGCCGAATTT TAGGCCGGCC
   241 GCGCCTACAA AGGTACGGGG GGCCAATATC CGCTTCCCAA GCCACGTTGC AGTTGCCCCA
   301 TAACAGAACA AAGGCATCAT GGTGGGAGCG ACGCTGTGGC TGACGCCCAG GCAGACGTGC
   361 CCTCGACCTA ATGGCCTTGG GCGCAACTTG CGTTCAAAGA CTCGATGGTT CACGGGATTC
   421 TGCAATTCAC ACCAAGTATC GCATTTCGCT ACGTTCTTCA TCGATGCGAG AGCCGAGATA
   481 TCCATTGCCG AGAGTCGTTA TAAGATCGGA ATTACAACAT CGTCATGAAG ACGTGCTCTA
   541 TCCGTTAAGA TTTTCCTTGG CGCAGACCGC GCCGAGTTGT TATTTGAATC AACGAGGGAC
   601 GTCGTTGTCG CTTTCACGAC ACAATCGTCC CAAGTGACCC AGTAGGAAGG ATTCAAGGTT
   661 AACACCCTTC GTCCCTCCCA TAAGTGTTTT TCACAAGTTC GCTGGTCGTT CTGCTTTGCA
   721 GGTTTTGACA ATGATCCTTC CGCAGGTTCA CTACGGAAAC CTTGTTACGA CTTCTCCTTC
   781 CTCTAAATGA TAAGGTTCAA TGGACTTCTC GCGACGTCGC CGGCGGCGAA CCACCCACGT
   841 CGCCGCGATC CGAACATTTC ACCGGACCAT TCAATCGGTA GGAGCGACGG GCGGTGTG
```

Figure 13K

```
Tulipa edulis
    CGTAACAAGG TTTCCGTAGT GAACCTGCGG AAGGATCATT GTCGATACCC GACCGAAAGA
    CCGTGAACTG TAACGGATGT CACAGGGTTG TCGGGCAAGC TCGGCCTCCC TGGAGCCCTA
    CCGCCCCCTT TCGGAGCGAC CTTGTGCCGC GCGGATGGGG TGGTACGGGA TAACGAAACC
    CCGCGCTGCA TGCGCCAAGG AACATATATG ACCGGATGGA CGTCTGCCTT TGCCCTTGCG
    GCGAGGCAAC GACCGCTGAA CATTACCATA CGACTCTCGG CAACGGATAT CTCGGCCTCT
    CACATCGATG AAGAACGTAG CGAAATGCGA TACTTGGTGT GAATTGCAGA ATCC
    GTGAACCATC GAGTTTTTGA CGCAAGTTGC GCCCGAGGCC TTTCCGGCTG AGGGCACGCC
    TGCCTGGGCG TCACGCCTCG CGTCGCTCTA TGCTCCTGAC CCTTCAGGGC GGTGGTGTTG
    ATGCGGAAAT TGGCCCCCCG TACCTTGTGT GCGGTGGGCT AAAGAGAGGG CTGCCAGCCA
    GGTGTGGCAC GGCAAGTGGT GGACATAGCG CCAGCAGGAT GCCGTGGCCC CCCTAGCTGG
    ATGGACCTAA GTACCCGGAT AAGGTGAGAC GCACTCCTGT ATGGGATTGT ATTGTCGCCT
    CGCAAAGCGA CCCCAGGTCA GGCGGGGACA CCCGCTGAGT TTAAGCATAT CAATAAGCGG
    AGGAAAAGAA ACTAACAAGG ATTCCCCTAG TAACGGCGAG
```

Figure 13L

```
Pheretima aspergillus 18S rp DNA
    1 CCGCCCGTGG CTCCTACCGA TTGGATGTTT TAGTGAGATC CTCGGATTGG ACCCGGCGCG
   61 GAGGGCAACC TTCGGGTCGG TGTTCCGAAA AGACGATCAN ACTTGATCAT CTAGAGGAAG
  121 TAAAAGTCGT ACAAGGTTTC CGTAGGTGAA CCTGCGGAAG GATCATTACC GTAACGCTCG
  181 CTCGCTCGGA AGGCTCGCCC GCCGACGCGA CGCAGCAGTC AAACGAGTCA CACACGGGAA
  241 TCGAACGGCC GCGGTTCCAC AAGCGTCCGG TCCCGAAAGG ACGGACGGCG GTCGACAGAA
  301 GACGACCGTG CGTCCCCGAG CGTCACGTGG AATCGATCGG CGGGCTTACC AGTGTCTAGA
  361 CGCAGTGGGT ACCTCTCCGT TCGCCGCCCC GAGCCGGTCG GCGACGGGGA GAGCATTGGC
  421 GGTCGGCGAT CGTCGTGAGG CATCCGATGC CTGCGGCGTC GTACGCTGTC GTTTATGCGA
  481 GGTTCAAAGA GCCGCGCTAA CCGTTCGTCT CGTCCGCCGA CGAGCGGCGG CCGCCCCGCG
  541 TTGTTTTTTC TCAAACCTAA TTTTTAAGAC ACCGAACGTG GTGAACGTTT CCAGTCTGGC
  601 CGTTGCGCCG CTTCGGCGGC TCGGTCGACC GTCTTCGAAG GAGAAGGCGA ACGTGAAAAA
  661 CACTCTTGGC GGTGGATCAC TCGGTTCGTG CGTCGATGAA GAGCGCAGCC AGCTGCGTTA
  721 ATTAATGTGA ATTGCAGGAC ACATTGAACA TCGAGATCTT GAACGCATAT TGCGGCCTCG
  781 GGCACTCCCG AGGCCACGCC CGTCTCAGGG TCGGTTGAAA ATCGAATCGC GAGTGCTCTC
  841 CGCTCGCGCA TTGACAGTC GCAGACGGCG ATCGCGACGA AGTGGAGGCG TGCTGCCCGA
  901 TCGGTGGCCG CTTTTCTTCG TCGTCGCGAG ACCCGGTCTT CGTCGTCCGA AGAACAGACG
  961 CGTGGCTCAC TCGCTTGCCG CCGGATCGGC GCGGCGGGAG CGGGACGGCG AGTCGGATTC
 1021 TTTGCTCGTC GCCTCTCGCC TCGCGTCGTG CAGGCTTTCG TGCGACGGCA GCGAGGTCGC
 1081 GCAACGTCGT GATCCATCTT CGACCTGAGA TCGGACGAGA TTACCCACTG AATTAAAGCA
 1141 TATTAATAAG CGGAGGAAAA GAAACTAACG AGGATTCCCC TAGTAACGGC GAG
```

Figure 14

| CLASS | Magnoliopsida (Dicot Plants) | | | |
|---|---|---|---|---|
| SUB-CLASS | Rosidae | Asteridae | Asteridae | Asteridae |
| ORDER | Cornales | Campanulales | Campanulales | Campanulales |
| FAMILY | Araliaceae | Asteridae | Asteridae | Asteridae |
| GENUS | *Panax* | *Codonopsis* | *Campanulaceae* | *Platycodon* |
| SPECIES | 5 | 4 | 1 | 1 |

| CLASS | Magnoliopsida (Dicot Plants) | | |
|---|---|---|---|
| SUB-CLASS | Hamamelididae | Caryophyllidae | Caryophyllidae |
| ORDER | Ranales | Chenopodiales | Chenopodiales |
| FAMILY | Berberidaceae | Nyctaginaceae | Phytolaccaceae |
| GENUS | *Epimedium* | *Mirabilis* | *Phytolacca* |
| SPECIES | 4 | 1 | 1 |

| CLASS | Liliopsida (Monocot Plants) |
|---|---|
| SUB-CLASS | Liliidae |
| ORDER | Liliales |
| FAMILY | Liliaceae |
| GENUS | *Tulipa* |
| SPECIES | 1 |

SEQUENCE LISTING

<160> NUMBER OF SEQ ID NOS: 27

<210> SEQ ID NO 1
<211> LENGTH: 875
<212> TYPE: DNA
<213> ORGANISM: P. Quinquefolius

<400> SEQUENCE: 1

```
actcgccgtt actaggggaa tccttgtaag tttcttttcc tccgcttatt gatatgctta      60
aactcagcgg gtagtcccgc tgacctgggg tcgcggtcgg agcgcacgtc gaggacggcg     120
caacagggtc atgagagctt ttgctggcga cgggtcaccg cacgacatga aagagggct     180
ttttacaacc accacttgtc gtgacgtcca tcgccaagga ctcgcatttg gccaaccgc     240
gcggtgagac acggaggcc attatccgcc cctccgcctc aactcccgca agggagtgat     300
ggggttgggggg gcgacgcgat gcgtgacgcc caggcagacg tgccctcggc ctaatggctt     360
cgggcgcaac ttgcgttcaa agactcgatg gttcacggga ttctgcaatt cacaccaagt     420
atcgcatttc gctacgttct tcatcgatgc gagacgcgag atatccgttg tcgagagtcg     480
tttgtgtttt agaaagacgc ttccgccgcc cgcaaacggg ggggacgcgt gcagttcagt     540
ttgatttcct tggcgcattc cgcgccgggg ggtcgttgtt cggacgagat ccacccaagg     600
gtggtccccg accatgggtt tgcaacttgg ggagcttgcg caccctcgt ccctcacccg      660
gtattgtaac gtgttcgcgg gtcgttctgc tatgcaggtt tcgacaatga tccttccgca     720
ggttcaccta cggaaacctt gttacgactt ctccttcctc taaatgataa ggttcagtgg     780
acttctttcg acgtcgcggg cagcgaaccg cccacgtcgc cgcaatccga acacttcacc     840
ggaccattca atcggtagga gcgacgggcg gtgtg                                875
```

<210> SEQ ID NO 2
<211> LENGTH: 874
<212> TYPE: DNA
<213> ORGANISM: P. Ginseng

<400> SEQUENCE: 2

```
actcgccgtt actaggggaa tccttgtaag tttcttttcc tccgcttatt gatatgctta      60
aactcagcgg gtagtcccgc tgacctgggg tcgcggtcgg agcgcacgtc gaggagcgca     120
acagggtcat gagagctttt gctggcgacg ggtcaccgca cgacatgaga agagggcttt     180
ttacaaccac cacttgtcgt gacgtccatc gccaaggact cgcatttggg ccaaccgcgc     240
ggtgagacac gggaggccat tatccgcccc tccgcctcga ctcccgcaaa ggagtgatgg     300
gttgggggggc gacgcgatgc gtgaacgccc aggcagacgt gccctcggcc taatggcttc     360
```

-continued

```
gggcgcaact tgcgttcaaa gactcgatgg ttcacgggat tctgtaattc acaccaagta    420
tcgcatttcg ctacgttctt catcgatgcg agagccgaga tatccgttgc cgagagtcgt    480
ttgtgtttta gaaagacgct tccgccgccc gcaaacgggg gggacgcgtg cagttcagtt    540
tgatttcctt ggcgcattcc gcgccggggg gtcgttgttc ggacgagagc cacccaaggg    600
tggtccccga ccatgggttt gcaacttggg gagcttgcgc acccctcgtc cctcacccgg    660
tattgtaacg tgttcgcggg tcgttctgct atgcaggttt cgacaatgat ccttccgcag    720
gttcacctac ggaaaccttg ttacgacttc tccttcctct aaatgataag gttcagtgga    780
cttctttcga cgtcgcgggc agcgaaccgc ccacgtcgcc gcaatccgaa cacttcaccg    840
gaccattcaa tcggtaggag cgacgggcgg tgtg                                874
```

<210> SEQ ID NO 3
<211> LENGTH: 875
<212> TYPE: DNA
<213> ORGANISM: P. Ginseng

<400> SEQUENCE: 3

```
actcgccgtt actaggggaa tccttgtaag tttcttttcc tccgcttatt gatatgctta     60
aactcagcgg gtagtcccgc tgacctgggg tcgcggtcgg agcgcacgtc gaggacggcg    120
caacagggtc atgagagctt tgctggcga cgggtcaccg cacgacatga aagagggct     180 ttttacaacc accacttgtc gtgacgtcca tcgccaagga ctcgcatttg ggccaaccgc    240
gcggtgagac acggaggcc attatccgcc cctccgcctc aactcccgca agggagtgat    300
gggttggggg gcgacgcgat gcgtgacgcc caggcagacg tgccctcggc ctaatggctt    360
cgggcgcaac ttgcgttcaa agactcgatg gttcacggga ttctgcaatt cacaccaagt    420
atcgcatttc gctacgttct tcatcgatgc gagacgcgag atatccgttg tcgagagtcg    480
tttgtgtttt agaaagacgc ttccgccgcc cgcaaacggg gggacgcgt gcagttcagt    540 ttgatttcct tggcgcattc gcgccgggg gtcgttgtt cggacgagat ccacccaagg    600
gtggtccccg accatgggtt tgcaacttgg ggagcttgcg caccctcgt ccctcacccg    660 gtattgtaac gtgttcgcgg gtcgttctgc tatgcaggtt tcgacaatga tccttccgca    720
ggttcaccta cggaaacctt gttacgactt ctccttcctc taaatgataa ggttcagtgg    780
acttctttcg acgtcgcggg cagcgaaccg cccacgtcgc gcaatccga acacttcacc    840 ggaccattca atcggtagga gcgacgggcg gtgtg                                875
```

<210> SEQ ID NO 4
<211> LENGTH: 870
<212> TYPE: DNA
<213> ORGANISM: P. Ginseng

<400> SEQUENCE: 4

```
actcgccgtt actaggggaa tccttgtaag tttcttttcc tccgcttatt gatatgctta     60
aactcagcgg gtagtccggc ctgacctggg gtcgcggtcg gagcgcacgt cgaggacggc    120 gcaacaggt catgagagct tttgctggcg acgggtcacc gcacgacatg aagagggc      180 tttttacaac caccacttgt cgtgacgtcc atcgccaagg actcgcattt gggccaaccg    240
cgcggtgaga cacggaggc cattatccgc cctccgcct caactcccgc aagggagtga    300
tgggttgggg gcgacgcga tgcgtgacgc ccaggcagac gtgccctcgg cctaatggct    360
tcgggcgcaa cttgcgttca aagactcgat ggttcacggg attctgcaat tcacaccaag    420
tatcgcattt cgctacgttc ttcatcgatg cgagagccga gatatccgtt gccgagagtc    480
```

```
gtttgtgttt tagaaagacg cttccgccgc ccgcaaacgg gggggacgcg tgcagttcag      540
tttgatttcc ttggcgcatt ccgcgccggg gggtcgttgt tcggacgaga tccacccaag      600
ggtggtcccc gaccatgggt ttgcaacttg gggagcttgc gcaccccteg tccctcaccc      660 ggtattgtaa cgtgttcgcg ggtcgttctg ctatgcaggt ttcgacaatg atccttccgc      720
aggttcacct acggaaacct tgttacgact tctccttcct ctaaatgata aggttcagtg      780
gacttctttc gacgtcgcga gcagcgaacc gcccacgtcg ccgcaatccg aacacttcac      840
cggaccattc aatcggtagg agcgacgggg                                       870

<210> SEQ ID NO 5
<211> LENGTH: 875
<212> TYPE: DNA
<213> ORGANISM: P. Japonicus

<400> SEQUENCE: 5
actcgccgtt actaggggaa tccttgtaag tttcttttcc tccgcttatt gatatgctta      60
aactcagcgg gtagtcccgc ctgacctggg gtcgcggtcg gagcgcacgt cgaggacggc      120
gcaacagggt catgagagct tttgttggcg aagggtcacc gcacgacatg agaagagggc      180
tttttacaac caccacttgt cgtgacgtcc atcgccaagg actcgcattt gggccaaccg      240
cacggtgaga cacgggaggc caatatccgc ccctccgcct cgactccgc aagggagtga      300 tggggttggg ggcgacgcga tgcgtgaacg cccaggcaga cgtgccctcg gcctaatggc      360
ttagggcgca acttgcgttc aaagactcga tggttcacgg gattctgcaa ttcacaccaa      420
gtatcgcatt tcgctacgtt cttcatcgat gcgagagccg agatatccgt tgccgagagt      480
cgtttgtgtt ttagaaagac gcttccgccg cccgcaaatg ggggggacgc gtgcagttca      540
gtttgatttc cttggcacat tccgcgccgg gggtcgttg ttcggacgag atccaccaag      600
ggtgtccccg accatgggtt tgcaacttgg ggagcttgcg cacgcctcgt ccctcacccg      660
gtattgtaac gtgttcacgg gtcgttctgc tatgcaggtt tcgacaatga tccttccgca      720
ggttcaccta cggaaacctt gttacgactt ctccttcctc taaatgataa ggttcagtgg      780
acttctttcg acgtcgcggg cagcgaaccc ccacgtcgc cgcaatccga acacttcacc      840
ggaccattca atcggtagga gcgacgggcg gtgtg                                 875

<210> SEQ ID NO 6
<211> LENGTH: 876
<212> TYPE: DNA
<213> ORGANISM: P. Notoginseng

<400> SEQUENCE: 6
actcgccgtt actaggggaa tccttgtaag tttcttttcc tccgcttatt gatatgctta      60
aactcagcgg gtagtcccgc tgacctgggg tcgcggtcg agcgcacgtc gaggacggcg      120
caacagggtc atgagagctt tgctggcga cgggtcaccg cacgacatga gaagagggct      180
ttttacaacc accacttgtc gtgacgtcca tcgccaagga ctcgcatttg gccaaccgc      240 gcggtgagac acggaggcc attatccgcc cctccgcctc gactccgca aggagtgat       300 gggttggggg cgacgcgat gcgtgaacgc ccaggcagac gtgccctcgg cctaatggct       360
tcgggcgcaa cttgcgttca aagactcgat gattcacggg attctgcaat tcacaccaag      420
tatcgcattt cgctacgttc ttcatcgatg cgagagccga gatatccgtt gccgagagtc      480
gtttgtgttt tagaaagacg cttccgccgc ccgcaaacgg gggggacgcg tgcagttcag      540
```

-continued

```
tttgatttcc ttggcgcatt ccgcgccggg gggtcgttgt tcggacgaga gccacccaag    600
ggtggtcccc gaccatgggt ttgcaacttg gggagcttgc gcacccctcg tccctcaccc    660
ggtattgtaa cgtgttcgcg gtcgttctg ctatgcaggt ttcgacaatg atccttccgc     720
aggttcacct acggaaacct tgttacgact tctccttcct ctaaatgata aggttcagtg    780
gacttctttc gacgtcgcag gcagcgaacc gcccacgtcg ccgcaatccg aacacttcac    840
cggaccattc aatcggtagg agcgacgggc ggtgtg                              876
```

<210> SEQ ID NO 7
<211> LENGTH: 875
<212> TYPE: DNA
<213> ORGANISM: P. Trifolium

<400> SEQUENCE: 7

```
actcgccgtt actaggggaa tccttgtaag tttcttttcc tccgcttatt gatatgctta     60
aactcagcgg gtagtcccgc ctgacctggg gtcgcggtcg gagcgcgcgt cggggacggc    120
gcaacagggt cgtgagagcc tttgccggcg acgggtcacc gcacgacttg agaagagggc    180 ttttacaac caccacttgt cgtgacgtcc gtcgccgagg actcgcattt gggccaaccg     240
cgcggttaga cacggaggc caatatccgc ccctccgcct cgactcccgt aagggagtga    300
tgggttgggg ggcgacgcga tgcgtgacgc ccaggcagac gtgccctcgg cctaatggct    360
tagggcgcaa cttgcgttca aagactcgat ggttcacggg attctgcaat tcacaccaag    420
tatcgcattt cgctacgttc ttcatcgatg cgagagccga gatatccgtt gccgagagtc    480
gtttgtgttt tagaaagacg cttccgccgc ccgcaaacgg ggggacgcg tgcagttcag     540 tttgatttcc ttggcgcatt ccgcgccggg gggtcgttgt tcggacgggg agcacccggg    600 ggcggcccc gaccatgggt tcggaacttg ggggcttgc gcacccttcg tccctcaccc      660
ggtgttgaaa cgtgttcgcg gtcgttctg ctgtgcaggt ttcgacaatg atccttccgc     720
aggttcacct acggaaacct tgttacgact tctccttcct ctaaatgata aggttcagtg    780
gacttctttc gacgtcgcgg cagcgaaccg cccacgtcgc cgcaatccga acacttcacc    840
ggaccattca atcggtagga gcgacgggcg gtgtg                               875
```

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8

```
agccatcctc gctgcccgcc acac                                            24
```

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9

```
actcgccgtt actaggggaa                                                 20
```

<210> SEQ ID NO 10
<211> LENGTH: 24
<212> TYPE: DNA
<213> ORGANISM: Artificial Sequence

```
<220> FEATURE:
<223> OTHER INFORMATION: Primer

<400> SEQUENCE: 10
cacaccgccc gtcgctccta ccga                                      24

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
actcgccgtt actagggaa                                            20

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
cacaccgccc gtcgctccta ccga                                      24

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
ttgcgttcaa agactcgatg                                           20

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
aaccatcgag tctttgaacg ca                                        22

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
actcgccgtt actagggaa                                            20

<210> SEQ ID NO 16
<211> LENGTH: 918
<212> TYPE: DNA
<213> ORGANISM: Codonopsis Modesta

<400> SEQUENCE: 16
cacaccgccc gtcgctccta ccgaaggacc ggtccgggtg tgttgggttc gcggcgacct    60
gggcggttcg ccgccggcga cgtcgcgaga agtccactga accttatcat ttagaggaag   120
```

-continued

```
gagaagtcgt aacaaggttt ccgtagtgaa cctgcggaag gatcattgtc gaaacctgca        180
cagcagaacg acccgcgaac acgtgaacaa caccggggac gcgggcttgc ccgtggcccc        240
ttgccgtcgg cgcatgcacc cgcccaacca cttggtggaa gggagcatgc gtgcgtcgtt        300
cggcgccaaa cgaaccccgc gcgatccgcg ccaaggaaaa cttaactcaa agagcgccac        360
gtcctcccgt cgccccgttc gcggtgtgcg cacggttggg tggtcgcttc ttagtgaaaa        420
acacaaacga ctctcggcaa cggatatctc ggctctcgca tcgatgaaga acgtagcgaa        480
atgcgatact tggtgtgaat tgcagaatcc cgtgaaccat cgagtctttg aacgcaagtt        540
gcgcccgaag ccgttagggc gagggcacgt ctgcatgggc gtcacgcatc gcgtcgcctc        600
ccttatgata attttgttta cgttaacaag taacggaaag ggggagcgga tactggcctc        660
ccgtgccttg cggcgcggct ggctcaaaac ggagtccccg cgaaggacgc acgacaagtg        720
gtggttgata acaacccctc gcgtcctatc gtgcgcacgt cctgcgatgg gttggctctc        780
gtgaccctga cgcgtctagg tctaagccta aggcgctccg accgcgaccc catgtcaggc        840
gggactaccc gctgagttta agcatatcaa taagcggagg aaaagaaact tacaaggatt        900
cccctagtaa cggcgagt                                                     918
```

<210> SEQ ID NO 17
<211> LENGTH: 918
<212> TYPE: DNA
<213> ORGANISM: Codonopsis Nervosa

<400> SEQUENCE: 17

```
cacaccgccc gtcgctccta ccgaaggacc ggtccgggtg tgttgggttc gcggcgacct         60
gggcggttcg ccgccggcga cgtcgcgaga agtccactga accttatcat ttagaggaag        120
gagaagtcgt aacaaggttt ccgtagtgaa cctgcggaag gatcattgtc gaaacctgca        180
cagcagaacg acccgcgaac acgtgaataa caccggggac gcgggattgc ccgtggccct        240
ttgccgtcgg cgcatgcacc cgcccaacca cttggtggaa gggagcatgc gtgcgtcgtt        300
cggcgccaaa cgaaccccgc gcgatccgcg ccaaggaaaa cttaactcaa agagcgccac        360
gtcctcccgt cgccccgttc gcggtgtgcg cacggttggg tggtcgcttc ttagtgaaaa        420
acacaaacga ctctcggcaa cggatatctc ggctctcgca tcgatgaaga acgtagcgaa        480
atgcgatact tggtgtgaat tgcagaatcc cgtgaaccat cgagtctttg aacgcaagtt        540
gcgcccgaag ccgttagggc gagggcacgt ctgcatgggc gtcacgcatc gcgtcgcctc        600
gtttatgata attttgttta cgttaacaag taacggaaag ggggagcgga tactggcctc        660
ccgtgccttg cggcgcggct ggctcaaaac ggagtccccg cgaaggacgc acgacaagtg        720
gtggttgata acaacccctc gcgtcctatc gtgcgcacgt cctgcgatgg gttggctctc        780
gtgaccctga cgcgtctagg tctaagccta aggcgctccg accgcgaccc catgtcaggc        840
gggactaccc gctgagttta agcatatcaa taagcggagg aaaagaaact tacaaggatt        900
cccctagtaa cggcgagt                                                     918
```

<210> SEQ ID NO 18
<211> LENGTH: 917
<212> TYPE: DNA
<213> ORGANISM: Codonopsis Pilosula

<400> SEQUENCE: 18

```
cacaccgccc gtcgctccta ccgaaggacc ggtccgggtg tgttgggttc gcggcgacct         60
gggcggttcg ccgccggcga cgtcgcgaga agtccactga accttatcat ttagaggaag        120
```

```
gagaagtcgt aacaaggttt ccgtagtgaa cctgcggaag gatcattgtc gaaacctgac      180
agcagaacga cccgcgaaca cgtgaacaac accggggacg cgggcttgcc cgtggcccct      240
tgccgtcggc gcatgcaccc gcccaaccac ttggtggaag ggagcatgcg tgcgtcgttc      300
ggcgccaaac gaaccccgcg cgatccgcgc caaggaaaac ttaactcaaa gagcgccacg      360
tcctcccgtc gccccgttcg cggtgtgcgc acggttgggt ggtcgcttct tagtgaaaaa      420
cacaaacgac tctcggcaac ggatatctcg gctctcgcat cgatgaagaa cgtagcgaaa      480
tgcgatactt ggtgtgaatt gcagaatccc gtgaaccatc gagtctttga acgcaagttg      540
cgcccgaagc cgttagggcg agggcacgtc tgcatgggcg tcacgcatcg cgtcgcctcc      600
cttatgataa ttttgtttac gttaacaagt aacggaaagg gggagcggat actggcctcc      660
cgtgccttgc ggcgcggctg gctcaaaacg agtccccgc gaaggacgca cgacaagtgg      720
tggttgataa caacccctcg cgtcctatcg tgcgcacgtc ctgcgatggg ttggctctcg      780
tgaccctgac gcgtctaggt ctaagcctaa ggcgctccga ccgcgacccc atgtcaggcg      840
ggactacccg ctgagtttaa gcatatcaat aagcggagga aaagaaactt acaaggattc      900
ccctagtaac ggcgagt                                                      917

<210> SEQ ID NO 19
<211> LENGTH: 918
<212> TYPE: DNA
<213> ORGANISM: Codonopsis Tangshen

<400> SEQUENCE: 19
cacaccgccc gtcgctccta ccgaaggacc ggtccgggtg tgttgggttc gcggcgacct       60
gggcggttcg ccgccggcga cgtcgcgaga agtccactga accttatcat ttagaggaag      120
gagaagtcgt aacaaggttt ccgtagtgaa cgtgcggaag gatcattgtc gaaacctgca      180
cagcagaacg acccgcgaac acgtgaacaa caccggggac gcgggcttgc ccgtggcccc      240
ttgccgtcgg cgcatgcacc cgcccaacca cttggtggaa gggagcatgc gtgcgtcgtt      300
cggcgccaaa cgaaccccgc gcgctccgcg ccaaggaaaa cttaactcaa agagcgccac      360
gtcctcccgt cgccccgttc gcggtgtgcg cacggttggg tggtcgcttc ttagtgaaaa      420
acacaaacga ctctcggcaa cggatatctc ggctctcgca tcgatgaaga acgtagcgaa      480
atgcgatact tggtgtgaat tgcagaatcc cgtgaaccat cgagtctttg aacgcaagtt      540
gcgcccgaag ccgttagggc gagggcacgt ctgcatgggc gtcacgcatc gcgtcgcctc      600
ccttatgata attttgttta cgttaacaag taacggaaag ggggagcgga tactggcctc      660
ccgtgccttg cggcgcggct ggctcaaaac ggagtccccg cgaaggacgc acgacaagtg      720
gtggttgata caaccctc gcgtcctatc gtgcgcacgt cctgcgatgg gttggctctc      780
gtgaccctga cgcgtctagg tctaagccta aggcgctccg accgcgaccc catgtcaggc      840
gggactaccc gctgagttta agcatatcaa taagcggagg aaaagaaact tacaaggatt      900
cccctagtaa cggcgagt                                                     918

<210> SEQ ID NO 20
<211> LENGTH: 815
<212> TYPE: DNA
<213> ORGANISM: Platycodon Grandiflorus

<400> SEQUENCE: 20
tagaggaagg agaagtcgta acaaggtttc cgtagtgcac ctgcggaagg atcagtgtcg       60
```

-continued

```
aaactgcaca gcagcgcgtt cgccaacgca tgaacaacac cggggtctcg ggcttgcccg        120
tggcgcctac gcgtcgccgc atgcacccat tcaaccactt ggtggaaggg agtatgagtg        180
cgtcgttcgg cggcaaacga accccgcgat ccattttaag gagaacttaa ctcaagcgta        240
gagctccacg tgtcatcccg tcgaaccgtt cgcggtgtcc gcacggttaa gtggtcgctt        300
cttagtgaaa agcaaacgac tgtcggcaac ggatatctcg gctctcgcat cgatgaagaa        360
cgtagcgaaa tgcgatactt ggtgtgaatt gcagaatacc gtgaaccatc gagcctttga        420
acgcaagttg cgcccgaagc cgttagggcg aaggcacgtc tgcatgggcg tcacgcatcg        480
cgtcgcctcc cattatgata gatttgtgta cgttaataag tcaatacagg aaggggggtg        540
cggatagagg cctcccgtgc ctagcggcgg cgtggctggc tcaaaacgga gttcccgcga        600
agggcgcacg acaagtgacg gtcgataaca accccgagct tcctatcgag cccacgtcct        660
gcgatgggtt ggcgctcgtg accctgacgc gtctaggtct catgctaagg cgctcagacc        720
gcgactccat gtcaggcggg actacccgct gagtttaagc atatcaataa gccgaggaaa        780
agaaacttac aagcattccc ctagtaacgg cgagt                                   815
```

<210> SEQ ID NO 21
<211> LENGTH: 904
<212> TYPE: DNA
<213> ORGANISM: Campanumoea Javanica Blume

<400> SEQUENCE: 21

```
cacaccgccc gtcgctccta ccgaaggacc ggtccgggtg tgttgggttc gcgccgacct         60
gggcggttcg ccgttggcga cgtcgcgaga agtccactga accttatcat ttagaggaag        120
gagaagtcgt aacaaggttt ccgtagagaa cctgcggaag gatcgttgtc gaaacctgca        180
cagcagaacg acccgcgaac acatgaacga caccggacgc gggcttgccc gtggcccatg        240
ccgtcggtcc atgcaccca acctcttggt ggaaatgagc atgcagtgcg taattcggcg        300
tcaaacgaac ctcgcgatcc gtgccaagga gcttaactcc aagagctcca cgtcctcccg        360
gcgcccgttc gcggtgtgcg tacggttggg tggtcgcttc ttagggaaaa actcaaacga        420 cttcggcaa cggatatctc gactctcgca tcgatgaaga acgtagcgaa atgcgatact        480
tggtgtgaat tgcagaatcc cgtgaaccat cgagtctttg aacgcaagtt ccgcccgaag        540
ccgttagggc gagggcgagt ctgcatgggc gccacgcatc gcgtcgctcc caccatgatg        600
cctttgttct gttatcgggc aacgcaacgt gggaagcgga tattggcccc ccgtacccttt        660 gtgcggcgtg gccttcaaaa cggcctcgcg aacgacgtac gatcagtggt ggttgataac        720 cccttttgcgt catatcgtgc gtacgtgttg cgatgggttg gctatcgtga ccctgacgcg        780
tctacgtaca agcctaacgc gttccgactg cgaccccatg tcaggcggga ctacccgctg        840
agtttaagca tatcaataag cggaggagaa gagacttaca aggattcccc tagtaacggc        900
gagt                                                                     904
```

<210> SEQ ID NO 22
<211> LENGTH: 898
<212> TYPE: DNA
<213> ORGANISM: Epimedium Brevicornum

<400> SEQUENCE: 22

```
actcgccgtt actaggggaa tccttgtaag tttcttctcc tccgcttatt gatatgctta        60
aactcagcgg gtagtcccgc tgacctgggg tcgcagagtg aatgtcgttt atacgacacg       120
caagggtcca tatggcccaa atagacgacg aaacaacacg ataccggtct atgacaaagg       180
```

```
ggttattcaa ccaccactga tcgtgacgct cgtcgccgag ggccgaattt taggccggcc    240
gcgcctacaa aggtacgggg ggccaatatc cgcttcccaa accacgttgc agttgcccga    300
taacaaaaca aaggcatcat ggtgggagcg acgctgtggc tgacgcccag gcagacgtgc    360
cctcgaccta atggccttgg gcgcaacttg cgttcaaaga ctcgatggtt cacgggattc    420
tgcaattcac accaagtatc gcatttcgct acgttcttca tcgatgcgag agccgagata    480
tccattgccg agagtcgtta taagatcgga attacaacat cgtcatgaag acgtgctcta    540
tccgttaaga ttttccttgg cgcagaccgc gccgagttgt tatttgaatc aacgaggggc    600
gtcgttctcg ctttcacgac acaatcgtcc caagtgaccc agtaggaagg attcaaggtt    660
agcacccttc gtccctccca caagtgtttt tcacaagttc gctggtcgtt ctgctttgca    720
ggttttgaca atgatccttc cgcaggttca ctacggaaac cttgttacga cttctccttc    780
ctctaaatga taaggttcaa tggacttctc gcgacgtcgc cggcggcgaa ccacccacgt    840
cgccgcgatc cgaacatttc accggaccat tcaatcggta ggagcgacgg gcggtgtg     898

<210> SEQ ID NO 23
<211> LENGTH: 898
<212> TYPE: DNA
<213> ORGANISM: Epimedium Koreanum

<400> SEQUENCE: 23
actcgccgtt actaggggaa tccttgtaag tttcttctcc tccgcttatt gatatgctta     60
aactcagcgg gtagtcccgc tgacctgggg tcgcagagtg aatgtcgttt atacgacacg    120
caagggtcca tatgcccaaa atagacgacg aaacaacacg ataccggtct atgacaaagg    180
ggttattcaa ccaccactga tcgtgacgct cgtcgccgag ggccgaattt taggccggcc    240
gcgcctacaa aggtacgggg ggccaatatc cgcttcccaa gccacgttgc agttgcccga    300
taacagaaca aaggcatcat ggtgggagcg acgctgtggc tgacgcccag gcagacgtgc    360
cctcgaccta atggccttgg gcgcaacttg cgttcaaaga ctcgatggtt cacgggattc    420
tgcaattcac accaagtatc gcatttcgct acgttcttca tcgatgcgag agccgagata    480
tccattgccg agggtcgtta taagatcgga attacaacat cgtcatgaag acgtgctcta    540
tccgttaaga ttttccttgg cgcagaccgc gccgagttgt tatttgaatc aacgaggggc    600
gtcgttgtcg ctttcacgac acaatcgtcc caagtgaccc agtaggaagg attcaaggtt    660
agcacccttc gtccctccca taagtgtttt tcacaagttc gctggtcgtt ctgctttgca    720
ggttttgaca atgatccttc cgcaggttca ctacggaaac cttgttacga cttctccttc    780
ctctaaatga taaggttcaa tggacttctc gcgacgtcgc cggcggcgaa ccacccacgt    840
cgccgcgatc cgaacatttc accggaccat tcaatcggta ggagcgacgg gcggtgtg     898

<210> SEQ ID NO 24
<211> LENGTH: 898
<212> TYPE: DNA
<213> ORGANISM: Epimedium Pubescens

<400> SEQUENCE: 24
actcgccgtt actaggggaa tccttgtaag tttcttctcc tccgcttatt gatatgctta     60
aactcagcgg gtagtcccgc tgacctgggg tcgcagagtg aatgtcgttt atacgacacg    120
caagggtcca tatgcccaaa atagacgacg aaacaacacg ataccggtct atgacaaagg    180
ggttattcaa ccaccactga tcgtgacgct cgtcgccgag ggccgaattt taggccggcc    240
```

-continued

```
gcgcctacaa aggtacgggg ggccaatatc cgcttcccaa gccacgttgc agttgcccga   300
taacagaaca aaggcatcat ggtgggagcg acgctgtggc tgacgcccag gcagacgtgc   360
cctcgaccta atggccttgg gcgcaacttg cgttcaaaga ctcgatggtt cacgggattc   420
tgcaattcac accaagtatc gcatttcgct acgttcttca tcgatgcgag agccgagata   480
tccattgccg agagtcgtta taagatcgga attacaacat cgtcatgaag acgtgctcta   540
tccgttaaga ttttccttgg cgcagaccgc gccgagttgt tatttgaatc aacgaggggc   600
gtcgttgtcg ctttcacgac acaatcgtcc caagtgaccc agtaggaagg attcaaggtt   660
agcacccttc gtccctccca taagtgtttt tcacaagttc gctggtcgtt ctgctttgca   720
ggttttgaca atgatccttc cgcaggttca ctacggaaac cttgttacga cttctccttc   780
ctctaaatga taaggttcaa tggacttctc gcgacgtcgc cggcggcgaa ccacccacgt   840
cgccgcgatc cgaacatttc accggaccat tcaatcggta ggagcgacgg gcggtgtg     898
```

<210> SEQ ID NO 25
<211> LENGTH: 898
<212> TYPE: DNA
<213> ORGANISM: Epimedium Wushanense

<400> SEQUENCE: 25

```
actcgccgtt actaggggaa tccttgtaag tttcttctcc tccgcttatt gatatgctta    60
aactcagcgg gtagtcccgc tgacctgggg tcgcagagtg aatgtcgttt acacgacacg   120
caagggtcca tatggcccaa atagacgacg aaacaacacg ataccggtct atgacaaagg   180
ggttattcaa ccaccactga tcgtgacgct cgtcgccgag ggccgaattt taggccggcc   240
gcgcctacaa aggtacgggg ggccaatatc cgcttcccaa gccacgttgc agttgcccca   300
taacagaaca aaggcatcat ggtgggagcg acgctgtggc tgacgcccag gcagacgtgc   360
cctcgaccta atggccttgg gcgcaacttg cgttcaaaga ctcgatggtt cacgggattc   420
tgcaattcac accaagtatc gcatttcgct acgttcttca tcgatgcgag agccgagata   480
tccattgccg agagtcgtta taagatcgga attacaacat cgtcatgaag acgtgctcta   540
tccgttaaga ttttccttgg cgcagaccgc gccgagttgt tatttgaatc aacgagggac   600
gtcgttgtcg ctttcacgac acaatcgtcc caagtgaccc agtaggaagg attcaaggtt   660
aacacccttc gtccctccca taagtgtttt tcacaagttc gctggtcgtt ctgctttgca   720
ggttttgaca atgatccttc cgcaggttca ctacggaaac cttgttacga cttctccttc   780
ctctaaatga taaggttcaa tggacttctc gcgacgtcgc cggcggcgaa ccacccacgt   840
cgccgcgatc cgaacatttc accggaccat tcaatcggta ggagcgacgg gcggtgtg     898
```

<210> SEQ ID NO 26
<211> LENGTH: 754
<212> TYPE: DNA
<213> ORGANISM: Tulipa Edulis

<400> SEQUENCE: 26

```
cgtaacaagg tttccgtagt gaacctgcgg aaggatcatt gtcgataccc gaccgaaaga    60
ccgtgaactg taacggatgt cacagggttg tcgggcaagc tcggcctccc tggagcccta   120
ccgcccccct tcggagcgac cttgtgccgc gcggatgggg tggtacggga taacgaaacc   180
ccgcgctgca tgcgccaagg aacatatatg accggatgga cgtctgcctt tgcccttgcg   240
gcgaggcaac gaccgctgaa cattaccata cgactctcgg caacggatat ctcggcctct   300
cacatcgatg aagaacgtag cgaaatgcga tacttggtgt gaattgcaga atccgtgaac   360
```

-continued

```
catcgagttt ttgacgcaag ttgcgcccga ggcctttccg gctgagggca cgcctgcctg      420
ggcgtcacgc ctcgcgtcgc tctatgctcc tgacccttca gggcggtggt gttgatgcgg      480
aaattggccc cccgtacctt gtgtgcggtg ggctaaagag agggctgcca gccaggtgtg      540
gcacggcaag tggtggacat agcgccagca ggatgccgtg gcccccctag ctggatggac      600
ctaagtaccc ggataaggtg agacgcactc ctgtatggga ttgtattgtc gcctcgcaaa      660 gcgacdcccag gtcaggcggg gacacccgct gagtttaagc atatcaataa gcggaggaaa      720
agaaactaac aaggattccc ctagtaacgg cgag                                 754
```

<210> SEQ ID NO 27
<211> LENGTH: 1193
<212> TYPE: DNA
<213> ORGANISM: Pheretima Aspergillus
<220> FEATURE:
<221> NAME/KEY: misc_feature
<222> LOCATION: (100)..(100)
<223> OTHER INFORMATION: n = a, t, c, g, or u

<400> SEQUENCE: 27

```
ccgcccgtgg ctcctaccga ttggatgttt tagtgagatc ctcggattgg acccggcgcg       60
gagggcaacc ttcgggtcgg tgttccgaaa agacgatcan acttgatcat ctagaggaag      120
taaaagtcgt acaaggtttc cgtaggtgaa cctgcggaag gatcattacc gtaacgctcg      180
ctcgctcgga aggctcgccc gccgacgcga cgcagcagtc aaacgagtca cacacgggaa      240
tcgaacggcc gcggttccac aagcgtccgg tcccgaaagg acggacggcg gtcgacagaa      300
gacgaccgtg cgtccccgag cgtcacgtgg aatcgatcgg cgggcttacc agtgtctaga      360
cgcagtgggt acctgtccgt tcgccgcccc gagccggtcg gcgacgggga gagcattggc      420
ggtcggcgat cgtcgtgagg catccgatgc ctgcggcgtc gtacgctgtc gtttatgcga      480
ggttcaaaga gccgcgctaa ccgttcgtct cgtccgccga cgagcggcgg ccgccccgcg      540
ttgttttttc tcaaacctaa tttttaagac accgaacgtg gtgaacgttt ccagtctggc      600
cgttgcgccg cttcggcggc tcggtcgacc gtcttcgaag gagaaggcga acgtgaaaaa      660
cactcttggc ggtggatcac tcggttcgtg cgtcgatgaa gagcgcagcc agctgcgtta      720
attaatgtga attgcaggac acattgaaca tcgagatctt gaacgcatat tgcggcctcg      780
ggcactcccg aggccacgcc cgtctcaggg tcggttgaaa atcgaatcgc gagtgctctc      840
cgctcgcgca ttggacagtc gcagacgcg atcgcgacga agtggaggcg tgctgcccga      900
tcggtggccg ctttctttcg tcgtcgcgag acccggtctt cgtcgtccga agaacagacg      960
cgtggctcac tcgctcgccg ccggatcggc gcggcgggag cgggacggcg agtcggattc     1020
tttgctcgtc gcctcccgcc tcgcgtcgtg caggctttcg tgcgacggca gcgaggtcgc     1080
gcaacgtcgt gatccatctt cgacctgaga tcggacgaga ttacccactg aattaaagca     1140
tattaataag cggaggaaaa gaaactaacg aggattcccc tagtaacggc gag            1193
```

POLYMERASE CHAIN REACTION-RESTRICTION FRAGMENT LENGTH POLYMORPHISM TEST FOR THE AUTHENTICATION OF HERBAL CHINESE MEDICINES

This application is a continuation-in-part of U.S. Ser. No. 09/258,111, filed Feb. 25, 1999 now abandoned, which is a continuation of 08/778,912, filed Jan. 3, 1997 now U.S. Pat. No. 5,876,977. The content of these two applications are incorporated into this application by reference.

FIELD OF THE INVENTION

This invention is directed to the authentication of herbal and animal Chinese medicinal materials based upon RFLP patterns of the PCR-amplified rDNA.

BACKGROUND OF THE INVENTION

Traditional Chinese medicine refers to the medicinal materials and clinical application of such materials in the framework of the theoretical and empirical parameters circumscribed by the Chinese people in the last 2–3 millennia. This medical system and many of the medicinal materials have spread to and have been adopted by other Oriental countries such as Japan and Korea and evolved into Oriental medicine in those countries. As a result, traditional Chinese medicine should not be limited to only the herbs and other natural products used in Chinese medicine, but also to Oriental medicine. Traditional Chinese medicine currently in mainland China also covers the practice and medicinal materials used by Tibetan, Mongolian and other ethnic minorities.

The herbs and other natural products (animals and minerals) used in Chinese medicine have been recorded in a) classical herbals, e.g. Bencao Gangmu 〈本草綱目〉 and Bencao Gangmu Shiyi 〈本草綱目拾遺〉 the two together contain about 2,500 items; b) pharmacopoeia, e.g. Pharmacopoeia of the People's Republic of China 〈中華人民共和國藥典〉 which contains some 600 items; and c) treaties, e.g. Encyclopedia of Chinese Materia Medica Zhongyao Dacidian 〈中葯大詞典〉, which contains 5,767 items.

Traditionally the authentication of Chinese herbs relied upon morphological and histological inspection. In many cases, such as in the authentication of different ginseng species, and in the authentication of Acorus species, this method is unreliable. An effective program of authentication of Chinese herbs is essential and central issue in the healthy development of the herbal industry. It provides a necessary protection for consumers, minimises unfair business competition and prevents the health hazard of many adulterants.

In plant, animals and insect nuclear genomes, genes for ribosomal RNA (rDNA) are normally clustered in an array of multiple tandemly repeated copies of the cistron of 18S-ITS1-5.8S-ITS2-28S (Hillis, D. M and Dixon, M. T., 1991, The Quarterly Review of Biology, 66: 411–453). The sequence separates the 18S and 5.8S rRNA genes is designated as ITS1 (Internal Transcribed Spacer 1) and the sequence between 5.8S and 28S is designated as ITS2. The coding regions of the three rDNA genes are highly conserved, whereas the sequence homology within the ITS1 and ITS2 regions are lower across the plant kingdom. Furthermore within a given individual organism or species, the rDNA sequence is usually very similar due to the homogenization of the sequence by gene conversion and crossing over. This invention takes advantage of these features of plant rDNA, and use PCR to amplify the DNA of ITS1-5.8S-ITS2 regions with the conserved DNA sequences flanking to the regions as primers, and explores the DNA polymorphism in different plant species within the ITS1-5.8S-ITS2 region as a mean of authentication.

The roots of *Panax quinquefolius* (American Ginseng) and *P. ginseng* (Oriental ginseng) are important herbal medicinal materials widely applied in the Orient as tonic, prophylactic and anti-aging agents. In recent years the American ginseng, cultivated mainly in Wisconsin, USA, and British Columbia and Ontario, Canada, enjoys increasing popularity as a health food in Western countries. The ginseng trade is a big industry, in 1993 Hong Kong imports more than HK$1,500 million worthy of American and Oriental ginsengs. The retail price of cultivated American ginseng is usually much more expensive than that of cultivated Oriental ginseng produced in China, and that prompts wild-spread practice of disguising Orient ginseng as American ginseng by dishonest merchants. Tremendous financial incentive is also responsible for the imitation or adulteration of ginsengs with some herbal products including several poisonous plants that bear morphological similarity with ginsengs. The two ginsengs also have different medical values and potency.

Both American and Oriental ginsengs, together with several important Chinese medicines including Sanchi (*P. notoginseng*), belong to the genus of Panax in the family of Araliaceae. American ginseng and Oriental ginseng have similar morphological appearance. Furthermore many commercial ginseng products exist in the forms of powder or shredded slice, rendering their authentication by morphological and histological methods difficult and unpractical. In recent years, techniques have been developed to authenticate ginseng samples by examination of their ginsenoside profiles (Lang, Z., Lou, W S. and But, P P H, 1993, J. Clin. Pharm. Sci., 2:133–143). However, the application of chemical analysis may be limited as the amount of ginsenosides are significantly affected by many environmental factors such as the storage condition, the freshness of the products and the different post-harvest processing. In addition, the chemical method demands large quantity of materials for proper analysis.

SUMMARY OF THE INVENTION

This invention is based upon the DNA polymorphism in the ITS1-5.8S-ITS2 region of rDNA. Accordingly, plant or animal genomic DNA was isolated and the ITS regions of rDNA were selectively amplified using pairs of primers that correspond to the consensus DNA sequence within the rDNA. The resultant PCR products were then subject to the fragmentation by selected restriction endonuclease to generate, after electrophoresis, discrete and species-specific RFLP patterns. Application of this invention to authenticate American ginseng from Oriental ginseng and several common adulterants are detailed as examples. This invention is suitable to authenticate herbal and animal materials used in traditional Chinese medicine and differentiate them from various adulterants.

BRIEF DESCRIPTION OF THE DRAWINGS

FIG. 1. ITS1-5.8S-ITS2 DNA sequence of *P. quinquefolius* (SEQ ID NO:1).

FIG. 2. (A). ITS1-5.8S-ITS2 DNA sequence of *P. ginseng* (SEQ ID NO:2). (B) G1 DNA is the same as the sequnece of *P. ginseng* (SEQ ID NO:3); the IC DNA is the sequence from a Russian cultivar of *P. ginseng*. The four variables between the two are underlined (SEQ ID NO:4).

FIG. 3. ITS1-5.8S-ITS2 DNA sequence of *P. japonicus* (SEQ ID NO:5).

FIG. 4. ITS1-5.8S-ITS2 DNA sequence of *P. notoginseng* (SEQ ID NO:6).

FIG. 5. ITS1-5.8S-ITS2 DNA sequence of *P. trifolium* (SEQ ID NO:7).

FIG. 6. 3' AGCCATCCTCGCTGCCCGCCACAC 5' (SEQ ID NO:8) 5' ACTCGCCGTTACTAGGGGAA 3' (SEQ ID NO:9)

The primers, 18d and 28cc, used to amplify ITS1-5.8S-ITS2 regions of the plant rDNA genes.

Figure 7:
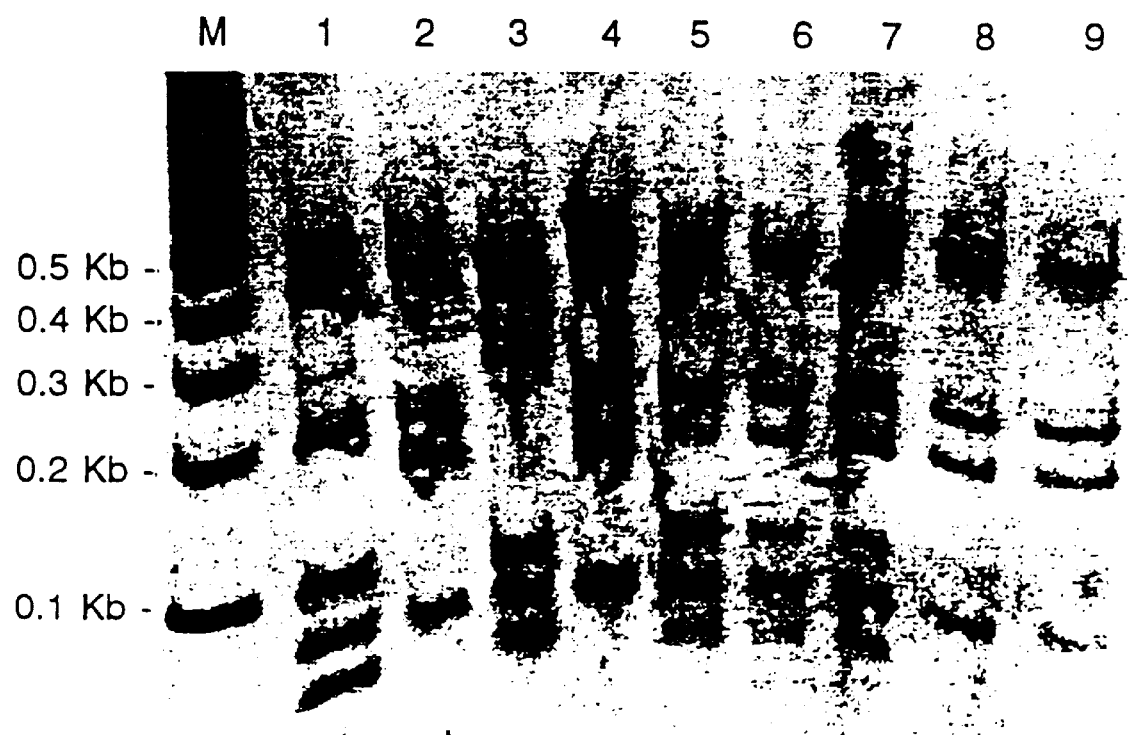

FIG. 7. The Hinf1 RFLP patterns of the ITS1-5.8S-ITS2 region for *P. quinquefolius* (American ginseng), *P. ginseng* (Oriental ginseng) and their adulterants. Lane M, DNA size marker;

lane 1, *P. quinquefolius* (American ginseng);

lane 2, *P. ginseng* (Oriental ginseng); lane 3, adulterant *Mirabilis jalapa*; lane 4, adulterant *Phytolacca acinosa*. Lanes 5 to 9 represent the RFLP patterns of the mixed samples of American ginseng and Oriental ginseng in different ratio. Lane 5, American Ginseng and Oriental ginseng in the ratio of 9:1; Lane 6, in the ratio of 7:3; Lane 7, in the ratio of 1:1; Lane 8, in the ratio of 3:7; and Lane 9, in the ratio of 1:9. Two fragments of 0.1 kb and 0.06 kb present in American ginseng but are absent from Oriental ginseng, while a fragment of 0.17 kb present in Oriental ginseng but absent from American ginseng. *M. jalapa* contains two characteristic fragments of 0.4 kb and 0.3 kb in size. The plant DNA were extracted using CTAB (cetyl triethylammonium bromide) method as described in Experimental Details and their rDNA ITS regions were amplified by PCR using the primers specified in FIG. 6. The resultant PCR products were subject to restriction of Hinf1, fractionated on PAGE and silver stained.

Figure 8:
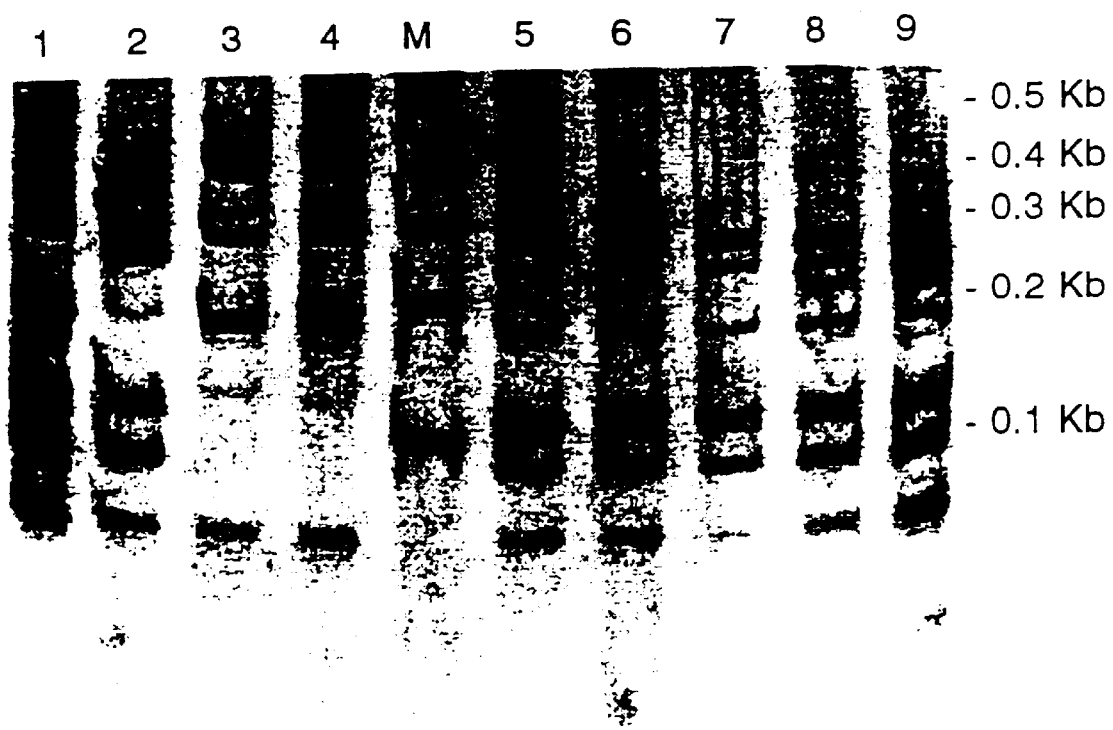

FIG. 8. The Taq1 RFLP patterns of the ITS1-5.8S-ITS2 region for *P. quinquefolius* (American ginseng), *P. ginseng* (Oriental ginseng) and their adulterants. Lane M, DNA size marker; lane 1, *P. quinquefolius* (American ginseng); lane 2, *P. ginseng* (Oriental ginseng); lane 3, adulterant *M. jalapa*; lane 4, adulterant *P. acinosa*. Lanes 5 to 9 represent the RFLP patterns of the mixed samples of American Ginseng and Oriental ginseng in different ratio. Lane 5, American ginseng and Oriental ginseng in the ratio of 9:1; Lane 6, in the ratio of 7:3; Lane 7, in the ratio of 1:1; Lane 8, in the ratio of 3:7; and Lane 9, in the ratio of 1:9. A 0.18 kb fragment is present in American ginseng but absent from oriental ginseng; while a 0.27 kb fragment is present in Oriental ginseng but absent from American ginseng. Both adulterants contain characteristic fragments of 0.28 kb and 0.4 kb in size. The plant DNA were extracted using CTAB method and their rDNA ITS regions were amplified by PCR using the primers specified in FIG. 6. The resultant PCR products were subject to restriction of Taq1, fractionated on PAGE and silver stained.

Figure 9:
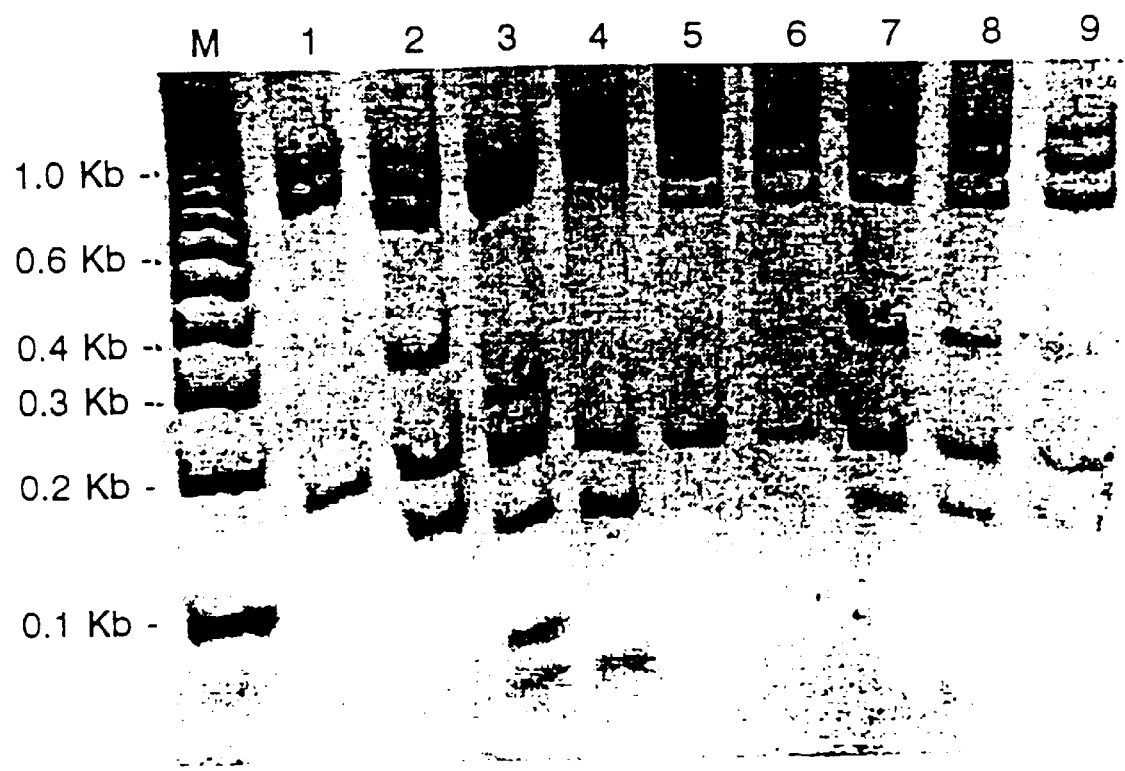

FIG. 9. The Sau3A1 RFLP patterns of the ITS1-5.8S-ITS2 region for *P. quinquefolius* (American ginseng), *P. ginseng* (Oriental ginseng) and their adulterants. Lane M, DNA size marker; lane 1, *P. quinquefolius* (American ginseng); lane 2, *P. ginseng* (Oriental ginseng); lane 3, adulterant *M. jalapa;* lane 4, adulterant *P. acinosa*. Lanes 5 to 9 represent the RFLP patterns of the mixed samples of American ginseng and Oriental ginseng in different ratio. Lane 5, American ginseng and Oriental ginseng in the ratio of 9:1; Lane 6, in the ratio of 7:3; Lane 7, in the ratio of 1:1; Lane 8, in the ratio of 3:7; and Lane 9, in the ratio of 1:9. When compared to American ginseng, Oriental ginseng contains two additional DNA fragments at the size of 0.6 kb and 0.17 kb. On the other hand, in comparison of ginsengs, *M. jalapa* contains three additional fragments of 0.3 kb, 0.07 kb and 0.05 kb in size, and *P. acinosa* contains an additional fragment of 0.05 kb in size. The plant DNA were extracted using CTAB method and their rDNA ITS regions were amplified by PCR using the primers specified in FIG. 6. The resultant PCR products were subject to restriction of Sau3A1, fractionated on PAGE and silver stained.

FIG. 10 Polymorphic restriction fragments among the four Epimedium species: *E. brevicornum, E. koreanum, E. pubescens*, and *E. wushanese*. * denotes absence of restriction sites. The polymorphic fragments are underlined.

FIG. 11 The PCR-RFLP patterns of Codonopsis rDNA ITS using restriction enzymes HinfI and HhaI. The PCR products were generated by primers 18d and 28cc, digested with restriction enzymes HinfI (panel A) and HhaI (panel B) and fractionated on 3.59 agarose gel. Lanes 1–6: *C. pilosula, C. tangshen, C. modesta, C. nervosa* var. *macrantha, Ca. javanica* Blume, and *P. grandiflorus*, respectively. M:100 bp molecular weight marker with a 800 bp intensive band indicated by an arrow.

Figure 12A:
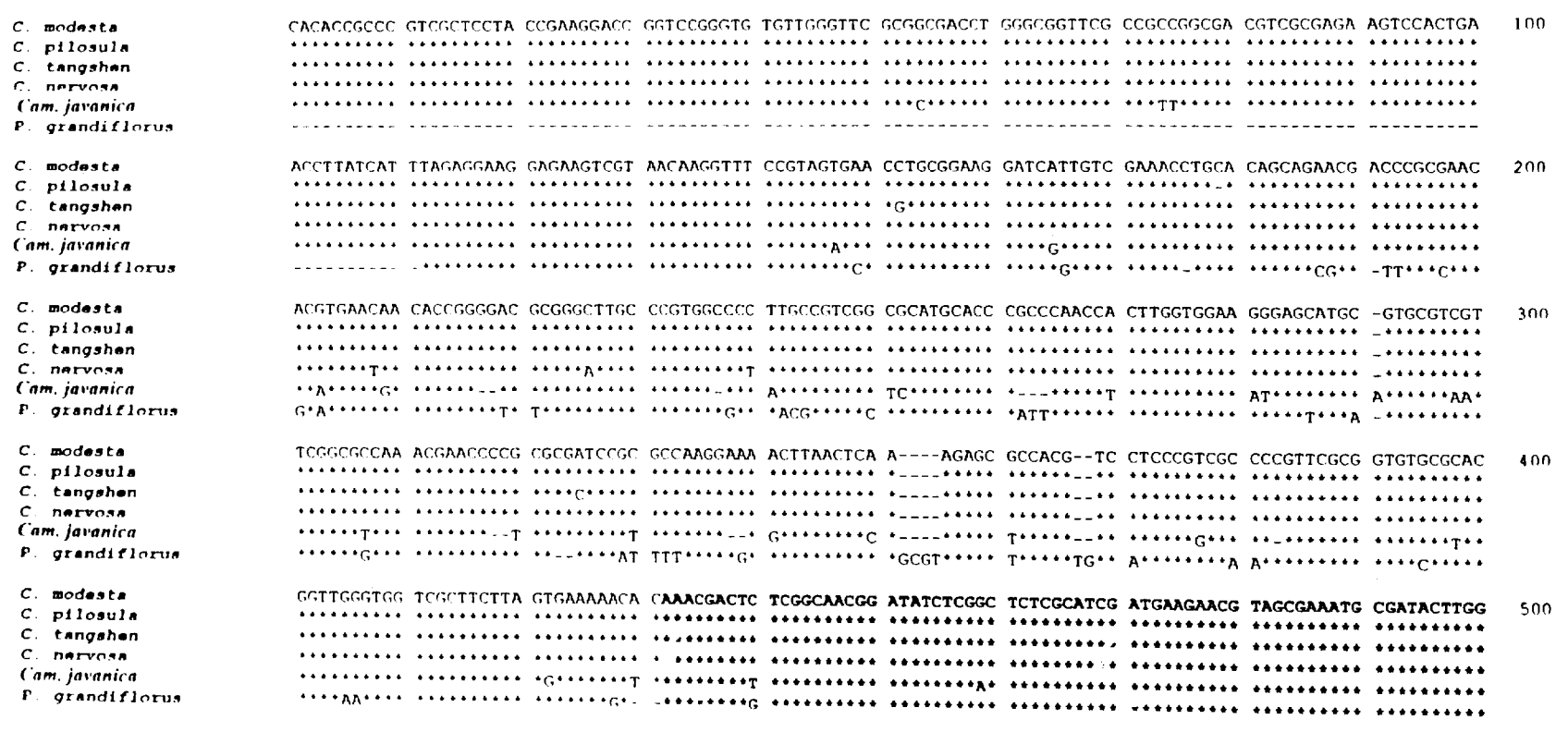
Figure 12B:
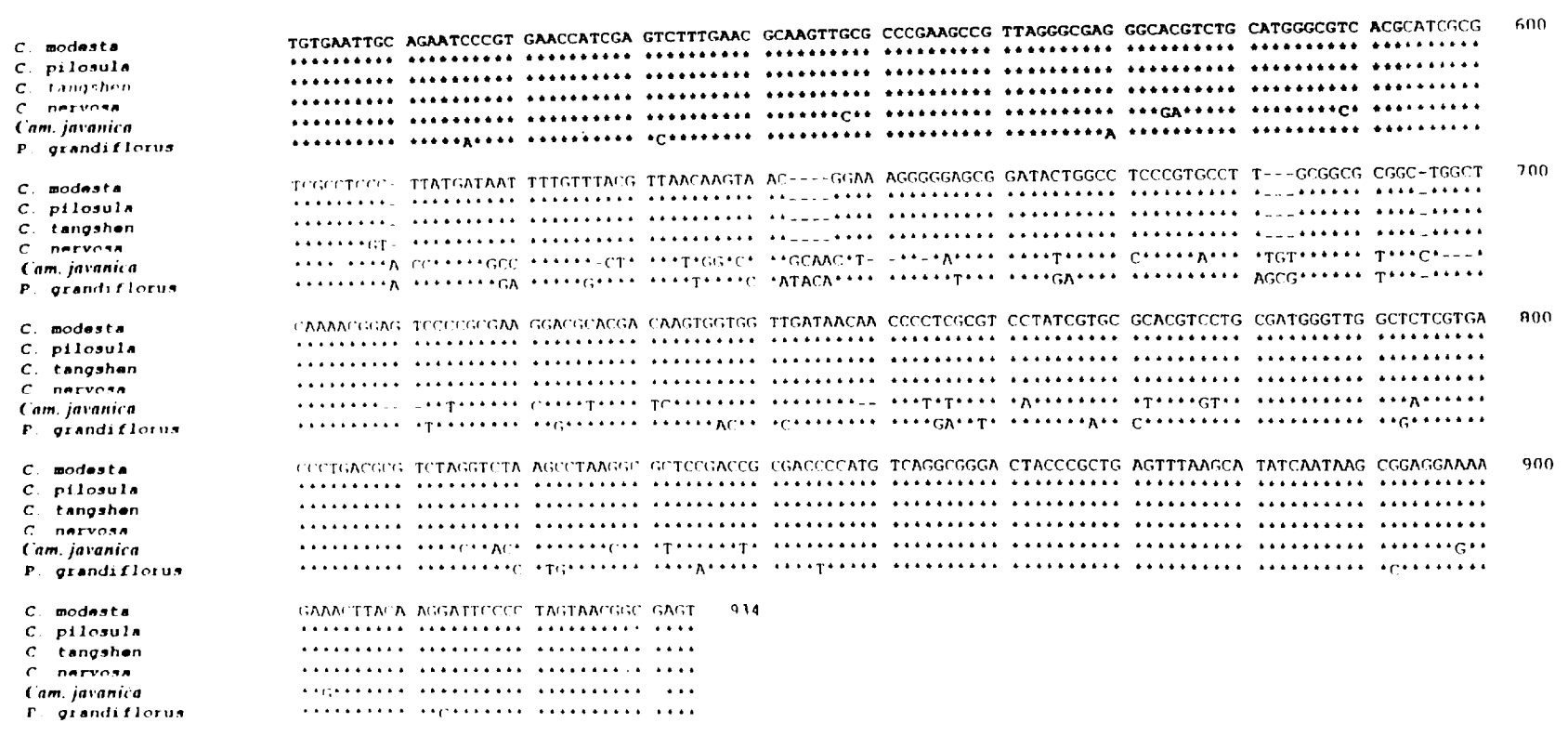

FIG. 12 DNA sequences of *C. pilosula, C. tangshen, C. modesta, C. nervosa* var *macrantha, Ca. javania* Blume and *P. grandiflorus* in the ITS1-5.8S-ITS2 region of nuclear ribosomal DNA. Position 1 is the 5' end of primer 18d. ITS1 region ranges from nucleotide 170 to 431, ITS2 region ranges from 594 to 839, and the 5.8S region is in bold type; hyphens denote alignment gaps.

FIG. 13 ITS1-5.8S-ITS2 DNA sequence of (A) *Codonopsis modesta* (SEQ ID NO:16)

(B) *Codonopsis nervosa* (SEQ ID NO:17)

(C) *Codonopsis pilosula* (SEQ ID NO:18)

(D) *Codonopsis tangshen* (SEQ ID NO:19)

(E) *Platycodon grandiflorus* (SEQ ID NO:20)

(F) *Campanumoea javanica* Blume (SEQ ID NO:21)

(G) *Epimedium brevicornum* (SEQ ID NO:22)

(H) *Epimedium koreanum* (SEQ ID NO:23)

(I) *Epimedium pubescens* (SEQ ID NO:24)

(J) *Epimedium wushanense* (SEQ ID NO:25)

(K) *Tulipa edulis* (SEQ ID NO:26)

(L) *Pheretima aspergillus* (SEQ ID NO:27)

FIG. 14 Taxonomic position of plant species whose ITS1-5.8S-ITS2 sequences have been determined in this application.

DETAILED DESCRIPTION OF THE INVENTION

This invention provides an isolated nucleic acid having the ITS1-5.8S-ITS2 sequence. This invention also provides isolated nucleic acid molecules having the ITS1-5.8S-ITS2 sequence from plant cultivars. It is expected even within the same species, there will be a minor variation between them. Such variation may be up to 1% or less. It is intent of this invention to cover this variation. It is easily appreciated by a person of ordinary skill in the art that the claimed invention works the same with this variation.

This invention provides an isolated nucleic acid having the ITS1-5.8S-ITS2 sequence of *P. quinquefolius*.

This invention provides the above isolated nucleic acid, wherein the sequence is as set forth in FIG. 1.

This invention provides an isolated nucleic acid having the ITS1-5.8S-ITS2 sequence of *P. ginseng*.

This invention provides the above isolated nucleic acid, wherein the sequence is as set forth in FIG. 2A or 2B.

This invention provides an isolated nucleic acid having the ITS1-5.8S-ITS2 sequence of P. japonicus.

This invention provides the above isolated nucleic acid, wherein the sequence is as set forth in FIG. 3.

This invention provides an isolated nucleic acid having the ITS1-5.8S-ITS2 sequence of P. notoginseng.

This invention provides the above isolated nucleic acid, wherein the sequence is as set forth in FIG. 4.

This invention provides an isolated nucleic acid having the ITS1-5.8S-ITS2 sequence of P. trifolium.

This invention provides the above isolated nucleic acid wherein the sequence is as set forth in FIG. 5.

This invention provides a method for authenticating the identity of herbs comprising the following steps:
(a) extracting rDNA from a herb sample with known identity determined by traditional means;
(b) amplifying the ITS1-5.8S-ITS2 region of the extracted rDNA using oligonucleotide primers that are conserved across plant kingdom and that flank to the ITS1-5.8S-ITS2 region by polymerase chain reaction;
(c) digesting the amplified ITS1-5.8S-ITS2 region with appropriate restriction endonucleases to generate restriction fragments; and
(d) separating the restriction fragments resulted from step (c) to generate profiles and comparing these profiles with the known profiles from an authenticated sample with the same identity, wherein similar profiles confirm the identity of the herbal sample.

This invention provides a method for identifying a herbal material comprising the following steps:
(a) extracting rDNA from the herbal material;
(b) amplifying the ITS1-5.8S-ITS2 region of the extracted rDNA using oligonucleotide primers that are conserved across plant kingdom and that flank to the ITS1-5.8S-ITS2 region by polymerase chain reaction;
(c) digesting the amplified ITS1-5.8S-ITS2 region with appropriate restriction endonucleases to generate restriction fragments; and
(d) separating the restriction fragments resulted from step (c) to generate a profile of the herbal material and comparing this profile with known profiles from different herbs, wherein the showing of similar profile with a known herb identifies the herbal material.

This invention provides an isolated nucleic acid having the ITS1-5.8S-ITS2 sequence.

This invention provides the above isolated nucleic acid, wherein the sequence is from an animal.

This invention provides a method for authenticating the identity of an animal traditional Chinese medicine comprising the following steps:
(a) extracting rDNA from an animal traditional Chinese medicine sample with known identity determined by traditional means;
(b) amplifying the ITS1-5.8S-ITS2 region of the extracted rDNA using oligonucleotide primers that are conserved across animal kingdom and that flank to the ITS1-5.8S-ITS2 region by polymerase chain reaction;
(c) digesting the amplified ITS1-5.8S-ITS2 region with appropriate restriction endonucleases to generate restriction fragments; and
(d) separating the restriction fragments resulted from step (c) to generate profiles and comparing these profiles with the known profiles from an authenticated sample with the same identity, wherein similar profiles confirm the identity of the sample.

This invention provides a method for identifying an animal traditional Chinese medicine comprising the following steps:
(a) extracting rDNA from the Chinese medicine;
(b) amplifying the ITS1-5.8S-ITS2 region of the extracted rDNA using oligonucleotide primers that are conserved across animal kingdom and that flank to the ITS1-5.8S-ITS2 region by polymerase chain reaction;
(c) digesting the amplified ITS1-5.8S-ITS2 region with appropriate restriction endonucleases to generate restriction fragments; and
(d) separating the restriction fragments resulted from step (c) to generate a profile of the herbal material and comparing this profile with known profiles from different known animal Chinese medicine sample, wherein the showing of similar profile with a known animal sample identifies the animal Chinese medicine.

This invention provides an isolated nucleic acid having the ITS1-5.8S-ITS2 sequence of Codonopsis modesta. In an embodiment, the sequence is as set forth in FIG. 13A (SEQ ID NO:16).

This invention provides an isolated nucleic acid having the ITS1-5.8S-ITS2 sequence of Codonopsis nervosa. In an embodiment, the sequence is as set forth in FIG. 13B (SEQ ID NO:17).

This invention provides an isolated nucleic acid having the ITS1-5.8S-ITS2 sequence of Codonopsis pilosula. In an embodiment, the sequence is as set forth in FIG. 13C (SEQ ID NO:18).

This invention provides an isolated nucleic acid having the ITS1-5.8S-ITS2 sequence of Codonopsis tangshen. In an embodiment, the sequence is as set forth in FIG. 13D (SEQ ID NO:19).

This invention provides an isolated nucleic acid having the ITS1-5.8S-ITS2 sequence of Platycodon grandiflorus. In an embodiment, the sequence is as set forth in FIG. 13E (SEQ ID NO:20).

This invention provides an isolated nucleic acid having the ITS1-5.8S-ITS2 sequence of Campanumoea javanica Blume. In an embodiment, the sequence is as set forth in FIG. 13F (SEQ ID NO:21).

This invention provides an isolated nucleic acid having the ITS1-5.8S-ITS2 sequence of Epimedium brevicornum. In an embodiment, the sequence is as set forth in FIG. 13G (SEQ ID NO:22).

This invention provides an isolated nucleic acid having the ITS1-5.8S-ITS2 sequence of Epimedium koreanum. In an embodiment, the sequence is as set forth in FIG. 13H (SEQ ID NO:23).

This invention provides an isolated nucleic acid having the ITS1-5.8S-ITS2 sequence of Epimedium pubescens. In an embodiment, the sequence is as set forth in FIG. 13I (SEQ ID NO:24).

This invention provides an isolated nucleic acid having the ITS1-5.8S-ITS2 sequence of Epimedium wushanense. In an embodiment, the sequence is as set forth in FIG. 13J (SEQ ID NO:25).

This invention provides an isolated nucleic acid having the ITS1-5.8S-ITS2 sequence of Tulipa edulis. In an embodiment, the sequence is as set forth in FIG. 13K (SEQ ID NO:26).

This invention provides an isolated nucleic acid having the ITS1-5.8S-ITS2 sequence of Pheretima aspergillus. In an embodiment, the sequence is as set forth in FIG. 13L (SEQ ID NO:27).

This invention provides an isolated nucleic acid having the ITS1-5.8S-ITS2 sequence of *Codonopsis modesta*.

This invention provides an isolated nucleic acid having the ITS1-5.8S-ITS2 sequence of *Codonopsis nervosa*.

This invention provides an isolated nucleic acid having the ITS1-5.8S-ITS2 sequence of *Codonopsis pilosula*.

This invention provides an isolated nucleic acid having the ITS1-5.8S-ITS2 sequence of *Codonopsis tangshen*.

This invention provides an isolated nucleic acid having the ITS1-5.8S-ITS2 sequence of *Platycodon grandiflorus*.

This invention provides an isolated nucleic acid having the ITS1-5.8S-ITS2 sequence of *Campanumoea javanica* Blume.

This invention provides an isolated nucleic acid having the ITS1-5.8S-ITS2 sequence of *Epimedium brevicornum*.

This invention provides an isolated nucleic acid having the ITS1-5.8S-ITS2 sequence of *Epimedium koreanum*.

This invention provides an isolated nucleic acid having the ITS1-5.8S-ITS2 sequence of *Epimedium pubescens*.

This invention provides an isolated nucleic acid having the ITS1-5.8S-ITS2 sequence of *Epimedium wushanense*.

This invention provides an isolated nucleic acid having the ITS1-5.8S-ITS2 sequence of *Tulipa edulis*.

This invention provides an isolated nucleic acid having the ITS1-5.8S-ITS2 sequence of *Pheretima aspergillus*.

This invention provides an isolated nucleic acid which consists of nucleotides, the sequence of which comprises the sequence set forth in SEQ ID NO: 16.

This invention provides an isolated nucleic acid which consists of nucleotides, the sequence of which comprises the sequence set forth in SEQ ID NO:17.

This invention provides an isolated nucleic acid which consists of nucleotides, the sequence of which comprises the sequence set forth in SEQ ID NO:18.

This invention provides an isolated nucleic acid which consists of nucleotides, the sequence of which comprises the sequence set forth in SEQ ID NO:19.

This invention provides an isolated nucleic acid which consists of nucleotides, the sequence of which comprises the sequence set forth in SEQ ID NO:20.

This invention provides an isolated nucleic acid which consists of nucleotides, the sequence of which comprises the sequence set forth in SEQ ID NO:21.

This invention provides an isolated nucleic acid which consists of nucleotides, the sequence of which comprises the sequence set forth in SEQ ID NO:22.

This invention provides an isolated nucleic acid which consists of nucleotides, the sequence of which comprises the sequence set forth in SEQ ID NO:23.

This invention provides an isolated nucleic acid which consists of nucleotides, the sequence of which comprises the sequence set forth in SEQ ID NO:24.

This invention provides an isolated nucleic acid which consists of nucleotides, the sequence of which comprises the sequence set forth in SEQ ID NO:25.

This invention provides an isolated nucleic acid which consists of nucleotides, the sequence of which comprises the sequence set forth in SEQ ID NO:26.

This invention provides an isolated nucleic acid which consists of nucleotides, the sequence of which comprises the sequence set forth in SEQ ID NO:27.

The nucleic acid of the subject invention may include DNA or RNA. The DNA may include genomic DNA or cDNA. The RNA may include MRNA and rRNA.

This invention provides a method for determining whether a given herbal or animal material is that of *Codonopsis modesta, Codonopsis nervosa, Codonopsis pilosula, Codonopsis tangshen, Platycodon grandiflorus, Campanumoea javanica, Epimedium brevicornum, Epimedium koreanum, Epimedium pubescens, Epimedium wushanense, Tulipa edulis*, or *Pheretima aspergillus*, which comprises:

a) extracting DNA from the herbal or animal materials;

b) amplifying an ITS1-5.8S-ITS2 region of the extracted rDNA using oligonucleotide primers whose nucleotide residue is conserved across the plant kingdom and which flank the ITS1-5.8S-ITS2 region of *Codonopsis modesta, Codonopsis nervosa, Codonopsis pilosula, Codonopsis tangshen, Platycodon grandiflorus, Campanumoea javanica, Epimedium brevicornum, Epimedium koreanum, Epimedium pubescens, Epimedium wushanense, Tulipa edulis*, and *Pheretima aspergillus*;

c) digesting amplified nucleic acid with one or more restriction endonucleases so as to generate restriction fragments;

d) separating the restriction fragments obtained in step c) to generate a restriction fragment length profile;

e) comparing this restriction fragment length profile with known restriction fragment length profiles of herbs and animals, thereby determining whether the material is that of either *Codonopsis modesta, Codonopsis nervosa, Codonopsis pilosula, Codonopsis tangshen, Platycodon grandiflorus, Campanumoea javania Blume, Epimedium brevicornum, Epimedium koreanum, Epimedium pubescens, Epimedium wushanense, Tulipa edulis*, or *Pheretima aspergillus* or whether the herbal or animal material is from an entirely different source.

This invention provides the above method wherein the extracted rDNA consists of nucleotides, the sequence of which comprises a sequence which includes but is not limited to SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, and SEQ ID NO:27.

This invention provides the above method wherein the extracted DNA consists of nucleotides, the sequence of which comprises the sequence set forth in SEQ ID NO:16.

This invention provides the above method wherein the extracted rDNA consists of nucleotides, the sequence of which comprises the sequence set forth in SEQ ID NO:17.

This invention provides the above method wherein the extracted rDNA consists of nucleotides, the sequence of which comprises the sequence set forth in SEQ ID NO:18.

This invention provides the above method wherein the extracted rDNA consists of nucleotides, the sequence of which comprises the sequence set forth in SEQ ID NO:19.

This invention provides the above method wherein the extracted rDNA consists of nucleotides, the sequence of which comprises the sequence set forth in SEQ ID NO:20.

This invention provides the above method wherein the extracted rDNA consists of nucleotides, the sequence of which comprises the sequence set forth in SEQ ID NO:21.

This invention provides the above method wherein the extracted rDNA consists of nucleotides, the sequence of which comprises the sequence set forth in SEQ ID NO:22.

This invention provides the above method wherein the extracted rDNA consists of nucleotides, the sequence of which comprises the sequence set forth in SEQ ID NO:23.

This invention provides the above method wherein the extracted rDNA consists of nucleotides, the sequence of which comprises the sequence set forth in SEQ ID NO:24.

This invention provides the above method wherein the extracted rDNA consists of nucleotides, the sequence of which comprises the sequence set forth in SEQ ID NO:25.

This invention provides the above method wherein the extracted rDNA consists of nucleotides, the sequence of which comprises the sequence set forth in SEQ ID NO:26.

This invention provides the above method wherein the extracted rDNA consists of nucleotides, the sequence of which comprises the sequence set forth in SEQ ID NO:27.

This invention provides an isolated nucleic acid molecule having the ITS1-5.8S-ITS2 sequence of P. quinquefolius. In an embodiment, this sequence is as set forth in FIG. 1.

In an embodiment, the ITS1-5.8S-ITS2 sequence is the DNA sequence between the oligonucleotide primers 18d and 28cc.

This invention provides an isolated nucleic acid molecule having the ITS1-5.8S-ITS2 sequence of P. ginseng. In an embodiment, the sequence is as set forth in FIG. 2A or B.

This invention provides an isolated nucleic acid molecule having the ITS1-5.8S-ITS2 sequence of P. japonicus. In one embodiment of the nucleic acid, the sequence is as set forth in FIG. 3.

This invention provides an isolated nucleic acid molecule having the ITS1-5.8S-ITS2 sequence of P. notoginseng.

In one embodiment of the nucleic acid, the sequence is as set forth in FIG. 4.

This invention provides an isolated nucleic acid molecule having the ITS1-5.8S-ITS2 sequence of P. trifolium. In an embodiment, the sequence is as set forth in FIG. 5.

This invention also provides a method for authenticating the identity of herbs comprising the following steps: (a) extracting DNA from a herb sample with known identity determined by traditional means; (b) amplifying the ITS1-5.8S-ITS2 region of the extracted DNA using oligonucleotide primers that are conserved across plant kingdom and that flank to the ITS1-5.8S-ITS2 region by polymerase chain reaction; (c) digesting the amplified ITS1-5.8S-ITS2 region with appropriate restriction endonucleases to generate restriction fragments; and (d) separating the restriction fragments resulted from step (c) to generate profiles and comparing these profiles with the known profiles from an authenticated sample with the same identity, wherein similar profiles confirm the identity of the herbal sample.

This invention further provides a method for identifying a herbal material comprising the following steps: (a) extracting DNA from the herbal material; (b) amplifying the ITS1-5.8S-ITS2 region of the extracted DNA using oligonucleotide primers that are conserved across plant kingdom and that flank to the ITS1-5.8S-ITS2 region by polymerase chain reaction; (c) digesting the amplified ITS1-5.8S-ITS2 region with appropriate restriction endonucleases to generate restriction fragments; and (d) separating the restriction fragments resulted from step (c) to generate a profile of the herbal material and comparing this profile with known profiles from different herbs, wherein the showing of similar profile with a known herb identifies the herbal material.

This invention provides an isolated nucleic acid molecule having the ITS1-5.8S-ITS2 sequence. In an embodiment, the sequence is from an animal.

This invention also provides a method for authenticating the identity of an animal traditional Chinese medicine comprising the following steps: (a) extracting DNA from an animal traditional Chinese medicine sample with known identity determined by traditional means; (b) amplifying the ITS1-5.8S-ITS2 region of the extracted DNA using oligonucleotide primers that are conserved across animal kingdom and that flank to the ITS1-5.8S-ITS2 region by polymerase chain reaction; (c) digesting the amplified ITS1-5.8S-ITS2 region with appropriate restriction endonucleases to generate restriction fragments; and (d) separating the restriction fragments resulted from step (c) to generate profiles and comparing these profiles with the known profiles from an authenticated sample with the same identity, wherein similar profiles confirm the identity of the animal traditional Chinese medicine.

This invention provides a method for identifying an animal traditional Chinese medicine comprising the following steps: (a) extracting DNA from the Chinese medicine; (b) amplifying the ITS1-5.8S-ITS2 region of the extracted DNA using oligonucleotide primers that are conserved across animal kingdom and that flank to the ITS1-5.8S-ITS2 region by polymerase chain reaction;(c) digesting the amplified ITS1-5.8S-ITS2 region with appropriate restriction endonucleases to generate restriction fragments; and (d) separating the restriction fragments resulted from step (c) to generate a profile of the herbal material and comparing this profile with known profiles from different known animal Chinese medicine sample, wherein the showing of similar profile with a known animal sample identifies the animal Chinese medicine.

Finally, this invention also provides a method for authentication of a given herbal or animal material which comprises:

a) extracting DNA from the herbal or animal material;

b) amplifying an ITS1-5.8S-ITS2 region of the extracted DNA using oligonucleotide primers whose nucleotide sequences are conserved across the plant or animal kingdoms and flank the ITS1-5.8S-ITS2 region;

c) digesting the mplified nucleic acid with one or more restriction endonucleases so as to generate restriction fragments;

d) separating the restriction fragments obtained in step c) to generate a restriction fragment length profile;

e) comparing the restriction fragment length profile obtained in step d) with a database of known restriction fragment length profiles of herbs and animals so as to thereby determine whether the material is one of the herbs or animals in the database or is from an entirely different source, thereby authenticating a given herbal or animal material.

In order to facilitate an understanding of the following examples, certain frequently occurring methods and/or terms are best described in Sambrook, et al. (Sambrook, et al. (1989)).

This invention will be better understood by reference to the Experimental Details section which follows, but those skilled in the art will readily appreciate that the specific experiments detailed are only illustrative of the invention as described more fully in the claims which follow thereafter.

Experimental Details

First Series of Experiments

Extraction of plant DNA. Dried roots of P. quinquefolius were from Canada, P. ginseng from China; M. jalapa L and P. acinosa Roxb from Hong Kong. The dried samples were rinsed with 70% ethanol and then distilled water to remove surface contaminants. The samples were then ground into fine powder in liquid nitrogen by a mortar and pestle. Powders of P. quinquefolius and P. ginseng were mixed in different proportion of 9:1, 7:3, 1:1, 3:7 and 1:9 in the mixed sampling assay. Ground sample powder was added into 12 vol. of 1×CTAB extraction buffer [50 mM Tris-HCl, pH 8.0, 0.7 M NaCl, 10 mM EDTA, 1% cetyl triethylammonium bromide (CTAB), 20 mM 2-mercaptoethanol] and incubated for 30 min at 56° C. with occasional shaking. The CTAB extraction buffer was pre-warmed to 56° C. The mixture was then cooled down to room temperature and extracted with an equal volume of chloroform/isoamyl alcohol (24:1). After centrifugation at 13,000×g for 10 min., 0.1 vol. of 10% CTAB solution was added to the aqueous phase. It was then extracted again with an equal volume of chloroform/isoamyl alcohol (24:1). The aqueous phase was collected, and added with an equal volume of 1×CTAB precipitation buffer [50 mM Tris-HCl, pH 8.0, 10 mM EDTA, 1% CTAB]. After standing at room temperature for 1 hour, the solution was centrifuged at 13,000×g for 15 min. The resultant pellet was resuspended in 400 ul 1 M NaCl, added with 800 ul of cooled absolute ethanol and stored at −20° C. overnight. The suspension was centrifuged at 13,000×g for 10 minutes and the pellet was washed with 70% ethanol twice. It was then dried and resuspended in 50 ul TE buffer [10 mM Tris-HCl, pH 8.0, 1 mM EDTA]. Further purification by CsCl gradient ultracentrifugation is optional.

Amplification of DNA. The plant rDNA was amplified using a pair of primers 18d and 28cc (Hillis, D. M and Dixon, M. T., 1991, The Quarterly Review of Biology, 66: 411–453), which correspond to the conserved regions of plant 18S and 28S rRNA respectively.

18d: 5'-CACAC CGCCC GTCGC TCCTA CCGA-3' (SEQ ID NO:10)

28cc: 5'-ACTCG CCGTT ACTAG GGGAA-3' (SEQ ID NO:11)

The reaction was performed in a 50 ul mixture containing 1 ng plant DNA, 1×Taq buffer [10 mM Tris-HCl, pH 8.3, 50 mM KCl, 0.001% gelatin], 0.2 mM dNTPs, 1.5 mM $MgCl_2$, 1 uM of each primer and 1 unit of Taq polymerase. Reaction mixtures were overlaid with mineral oil and reaction was carried out in a Thermolyne thermocycler. Initial template denaturation was programmed at 94° C., 5 min. It was then subjected to 35 cycles of 94° C. for 1 min.; 60° C. for 1 min.; 72° C. for 2 min., and with a final extension of 72° C. for 10 min. After the reaction, the products were resolved by a 1.4% TBE agarose gel.

Sequencing ITS1-5.8S-ITS2. The ITS1-5.8S-ITS2 region of plant DNA was sequenced in both strands using a set of primers on the conserved regions of the flanking 18S and 28S rDNA. The sequences of the primers used were as follows (Hillis, D. M and Dixon, M. T., 1991, The Quarterly Review of Biology, 66: 411–453):

```
18d:    CACAC CGCCC GTCGC TCCTA CCGA      (SEQ ID NO:12)

5.8c:   TTGCG TTCAA AGACT CGATG           (SEQ ID NO:13)

5.8d:   AACCA TCGAG TCTTT GAACG CA        (SEQ ID NO:14)

28cc:   ACTCG CCGTT ACTAG GGGAA           (SEQ ID NO:15)
```

SequiTherm™ Cycle Sequencing Kit (Epicentre, Madison, Wis.) was used to direct-sequence the PCR-amplified rDNA containing ITS-5.8S-ITS2. The sequencing procedure was done according to the manufacturers's instruction. The products were resolved onto a standard 8% polyacrylamide sequencing gel.

Determination of Restriction Fragment Length Polymorphism in the ITS1-5.8S-ITS2 region. Plant DNA amplified using primers 18d and 28cc was purified using Geneclean kit (Bio101, Inc.) and digested with selected restriction endonucleases TaqI, Sau3AI or HinfI. 1.5 ug rDNA was used for each digestion in a volume of 50 ul. For TaqI, a buffer of 100 mM NaCl, 10 mM Tris-HCl, 10 mM $MgCl_2$, 10 mM 2-mercaptoethanol, pH 8.4, supplemented with 100 ug/ml bovine serum albumin was used and the digestion was carried out at 65° C. for 4 hours. For Sau3AI, a buffer of 100 mM NaCl, 10 mM Tris-HCl, 10 MM $MgCl_2$, pH 7.3, supplemented with 100 ug/ml bovine serum albumin was used. For HinfI a buffer of 50 mM NaCl, 10 mM Tris-HCl, 10 mM $MgCl_2$, 1 mM dithiothreitol, pH 7.9 was used. The reaction for both Sau3AI and HinfI was incubated at 37° C. for 4 hours. The products were then purified by phenol: chloroform: isoamyl alcohol (25:24:1) and dissolved in 20 ul distilled water. They were resolved in a 5% PAGE and detected with Bio-Rad silver stain kit (Bio-Rad, Ltd)

Advantages of the Invention

The method of authentication of ginsengs described above are expected to be suitable for authentication of other herbal and animal traditional Chinese medicine as well, considering the existence of the conserved DNA sequences flanking to the ITS1-5.8S-ITS2 region in plant and animal kingdoms and the variation in the ITS1 and ITS2 regions among different species. As demonstrated in this application, ITS1-5.8S-ITS2 of more than 17 plant species belongs to diversified taxonomic groups (FIG. 14) can be readily isolated and authenticated using the method described here. We also demonstrated the feasibility of authentication of animal samples using the same method. In comparison to the existing procedures of authentication of traditional Chinese medicine, this invention provides the following advantages:

a. the authentication results are reliable and reproducible, and are not affected by the physical forms and age of the plant samples;

b. it is a method of high sensitivity: microgram sample is sufficient;

c. more than one distinctive profiles with different enzymatic digestion can be produced and that makes the interpretation of results straightforward;

d. the contamination of other biological materials can be detected.

References

Hillis, D. M and Dixon, M. T. (1991) Ribosomal DNA: molecular evolution and phylogenic inference. *Quar. Rev. Biol.*, 66: 411–453.

Lang, Z., Lou, W S. and But, P P H. (1993) High performance liquid chromatographical analysis of ginsenosides in *Panax ginseng* and *P. notoginseng. J. Clin. Pharm. Sci.*, 2:133–143.

Sambrook, et al. (1989) *Molecular Cloning: A Laboratory Manual.*

Second Series of Experiments

Extraction of Plant DNA

The dried roots of *Codonopsis pilosula, C. tangshen, C. modesta*, and *C. nervosa* var *macrantha*, as well as two related adulterants *Campanumoea javania* Blume and *Platycodon grandiflorus* were rinsed with 7% ethanol and then distilled water to remove surface contaminants. The samples were then ground into fine powder in liquid nitrogen by a mortar and pestle. Ground sample powder was added into 12 vol. of 1×CTAB extraction buffer [50 mM Tris-HCl, pH 8.0, 0.7 M NaCl, 10 mM EDTA, 1% cetyl triethylammonium bromide (CTAB), 20 mM 2-mercaptoethanol] and incubated for 30 min at 56° C. with occasional shaking. The CTAB extraction buffer was pre-warmed to 56° C. The mixture was then cooled down to room temperature and extracted with an equal volume of chloroform/isoamyl alcohol (24:1). After centrifugation at 13,000×g for 10 minutes, 0.1 vol. of 10% CTAB solution was added to the aqueous phase. It was then extracted again with an equal volume of chloroform/isoamyl alcohol (24:1). The aqueous phase was collected, and added with an equal volume of 1×CTAB precipitation buffer [50 mM Tris-HCl, ph 8.0, 10 mM EDTA, 1% CTAB]. After standing at room temperature for an hour, the solution was centrifuged at 13,000×g for 15 min. The resultant pellet was resuspended in 400 µl of 1M NaCl, added with 800 µl of cooled ethanol and stored at −20° C. overnight. The suspension was centrifuged at 13,000×g for 10 min and the pellet was washed with 70% ethanol twice. It was then dried and resuspended in 50 µl TE buffer (10 mM Tris-HCl, ph 8.0, 1 mM EDTA). Further purification by CsCl gradient ultracentrifugation is optional.

Amplification of DNA

The plant rDNA was amplified using a pair of primers 18d and 28cc (Hillis, D. M. and Dixon, M. T., 1991, the Quarterly Review of Biology, 66: 411–453), which correspond to the conserved regions of plant 18S and 28S respectively.

```
18d:      5'-CACACCGCCCGTCGCTCCTACCGA-3'

28cc:     5' ACTCGCCGTTACTAGGGGAA-3'
```

The reaction was performed in 50 µl mixture containing 1 ng plant DNA, 1×Taq buffer [10 mM Tris-HCl, pH 8.3, 50 mM Kcl, 0.001% gelatin], 0.2 mM dNTPs, 1.5 mM MgCl$_2$, 1 µM of each primer and 1 unit of Taq polymerase. Reaction mixtures were overlaid with mineral oil and reaction was carried out in a Thermolyne theremocycler. Initial template denaturation was programmed at 94° C., 5 min. It was then subjected to 35 cycles of 94° C. for 1 min.; 60° C. for 1 min.; 72° C. for 2 min., and with a final extension of 72° C. for 10 min. After the reaction, the products were resolved by a 1.4% TBE agarose gel.

Sequencing ITS1-5.8S-ITS2

The ITS1-5.8S-ITS2 region of the plant rDNA was sequenced in both strands using a set of primers on the conserved regions of the flanking 18S and 28S rDNA. The sequences of the primers used were as follows (Hillis, D. M. and Dixon, M. T., 1991, The Quarterly Review of Biology, 66:411–453):

```
18d:      CACACCGCCCGTCGCTCCTACCGA 5.8c:     TTGCGTTCAAAGACTCGATG 5.8d:     AACCATCGAGTCTTTGAACGCA

28cc:     ACTCGCCGTTACTAGGGGAA
```

SequiTherm™ Cycle Sequencing Kit (Epicentre, Madison, Wis.) was used to direct-sequence the PCR-amplified rDNA containing ITS-5.8S-ITS2. The sequencing procedure was done according to the manufacturer's instruction. The products were resolved onto a standard 8% of polyacrylamide sequencing gel.

Determination of Restriction Fragment Length Polymorphisms in the ITS1-5.8S-ITS2 Region Plant rDNA amplified using primers 18d and 28cc was purified using Geneclean kit (Bio101.Inc.) and digested with selected restriction endonucleases HhaI, or HinfI. 1.5 µg rDNA was used for each digestion in a volume of 50 µl. For HhaI, a buffer of 50 mM NaCl, 10 mM Tris-HCl, 10 mM MgCl$_2$, pH7.9 and 1 mM DTT was used. For HinfI, a buffer of 50 mM NaCl, 10 mM Tris-HCl, 10 mM MgCl$_2$, 1 mM dithiothreitol, pH 7.9 was used. The reaction for both HhaI and HinfI was incubated at 37° C. for 4 hours. The products were then purified by phenol: chloroform: isoamyl alcohol (25:24:1) and dissolved in 20 µl distilled water. They were resolved on 3.5% agarose gel.

Third Series of Experiments

Extraction of Animal DNA.

*Pheretima aspergillus* were rinsed with 70% ethanol and then distilled water to remove surface contaminants. The samples were then ground into fine powder in liquid nitrogen by a mortar and pestle. Ground sample powder (0.1 g) was added into 12 vol. of 1×CTAB extraction buffer (50 mM Tris-HCl, pH 8.0, 0.7M NaCl, 10 mM EDTA, 1% cetyl triethylammonium bromide (CTAB), 20 mM 2-mercaptoethanol) and incubated for 30 min at 56° C. with occasional shaking. The CTAB extraction buffer was pre-warmed to 56° C. with occasional shaking. The CTAB extraction buffer was pre-warmed to 56° C. The mixture was then cooled down to room temperature and extracted with an equal volume of chloroform/isoamyl alcohol (24:1). After centrifugation at 13,000×g for 10 min., 0.1 vol. of 10% CTAB solution was added to the aqueous phase. It was then extracted again with an equal volume of chloroform/isoamyl alcohol (24:1). The aqueous phase was collected, and added with an equal volume of 1×CTAB precipitation buffer (50 mM Tris-HCl, pH 8.0, 10 mM EDTA, 1% CTAB). After standing at room temperature for 1 hour, the solution was centrifuged at 13,000×g for 15 min. The resultant pellet was resuspended in 400 µl 1 M NaCl, added with 800 µl of cooled absolute ethanol and stored at −20° C. overnight. The suspension was centrifuged at 13,000×g for 10 min and the pellet was washed with 70% ethanol twice. It was then dried and resuspended in 50 µl TE buffer (10 mM Tris-HCl, pH 8.0, 1 mM EDTA). Further purification by CsCl gradient ultracentrifugation is optional.

Amplification of DNA

The animal rDNA was amplified using a pair of primers 18d and 28 cc (Hillis, D. M. and Dixon, M. T., 1991, The Quarterly Review of Biology, 66: 411–453), which correspond to the conserved regions of plant 18S and 28S respectively.

```
18d:     5' CACACCGCCCGTCGCTCCTACCGA 3'

28cc:    5' ACTCGCCGTTACTAGGGGAA 3'
```

The reaction was performed in a 50 µl mixture containing 1 ng animal DNA, 1×Taq buffer (10 mM Tris-HCl, pH 8.3, 50 mM KCl, 0.001% gelatin), 0.2 mM dNTPs, 1.5 mM MgCl$_2$, 1 µM of each primer and 1 unit of Taq polymerase. Reaction mixtures were overlaid with mineral oil and reaction was carried out in a Thermolyne thermocycler. Initial template denaturation was programmed at 94° C., 5 min. It was then subjected to 35 cycles of 94° C. for 1 min.; 60° C. for 1 min.; 72° C. for 2 min., and with a final extension of 72° C. for 10 min. After the reaction, the products were resolved by a 1.4% TBE agarose gel.

Sequencing ITS1-5.8S-ITS2

The ITS1-5.8S-ITS2 region of the animal rDNA was sequenced in both strands using a set of primers on the conserved regions of the flanking 18S and 28S rDNA. The sequences of the primers used were as follows (Hillis, D. M. and Dixon, M. T., 1991, The Quarterly Review of Biology, 66;411–453):

| | |
|---|---|
| 18d: | CACACCGCCCGTCGCTCCTACCGA |
| 5.8c: | TTGCGTTCAAAGACTCGATG |
| 5.8d: | AACCATCGAGTCTTTGAACGCA |
| 28cc: | ACTCGCCGTTACTAGGGGAA |

SequiTherm™ Cycle Sequencing Kit (Epicentre, Madison, Wis.) was used to direct-sequence the PCR-amplified rDNA containing ITS-5.8S-ITS2. The sequencing procedure was done according to the manufacturer's instruction. The products were resolved onto a standard 8% polyacrylamide sequencing gel.

What is claimed is:

1. A method for determining whether a given herbal or animal material is that of *Codonopsis modesta, Codonopsis nervosa, Codonopsis pilosula, Codonopsis tangshen, Platycodon grandiflorus, Campanumoea javanica, Epimedium brevicornum, Epimedium koreanum, Epimedium pubescens, Epimedium wushanense, Tulipa edulis,* or *Pheretima aspergillus*, which comprises:

a) extracting rDNA from the herbal or animal material;

b) amplifying an ITS1-5.8S-ITS2 region of the extracted rDNA using oligonucleotide primers whose nucleotide residue is conserved across the plant kingdom and which flank the ITS1-5.8S-ITS2 region of *Codonopsis modesta, Codonopsis nervosa, Codonopsis pilosula, Codonopsis tangshen, Platycodon grandiflorus, Campanumoea javanica, Epimedium brevicornum, Epimedium koreanum, Epimedium pubescens, Epimedium wushanense, Tulipa edulis,* and *Pheretima aspergillus;* c) digesting amplified nucleic acid with a restriction endonuclease so as to generate restriction fragments;

d) separating the restriction fragments obtained in step c) to generate a restriction fragment length profile;

e) comparing this restriction fragment length profile with known restriction fragment length profiles of herbs and animals, thereby determining whether the material is that of either *Codonopsis modesta, Codonopsis nervosa, Codonopsis pilosula, Codonopsis tangshen, Platycodon grandiflorus, Campanumoea javanica, Epimedium brevicornum, Epimedium koreanum, Epimedium pubescens, Epimedium wushanense, Tulipa edulis*, or *Pheretima aspergillus* or whether the herbal or animal material is from an entirely different source.

2. The method of claim 1, wherein the extracted rDNA comprises nucleotides, the sequence of which comprises a sequence selected from the group consisting of SEQ ID SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, and SEQ ID NO:27.

* * * * *

UNITED STATES PATENT AND TRADEMARK OFFICE
CERTIFICATE OF CORRECTION

PATENT NO.     : 6,309,840 B1
DATED          : October 30, 2001
INVENTOR(S)    : Jun Wang et al.

It is certified that error appears in the above-identified patent and that said Letters Patent is hereby corrected as shown below:

<u>Title page,</u>
Item [75], change the name of the second inventor from "Pang Chi Shaw" to -- Pang Chui Shaw --; and change the name of the third inventor from "Pui-Hay Paul But" to -- Paul Pui-Hay But --.
Item [73], Assignee, "Univerisity" should read -- University --.

Signed and Sealed this

Twelfth Day of November, 2002

*Attest:*

JAMES E. ROGAN
*Attesting Officer*   *Director of the United States Patent and Trademark Office*